(12) United States Patent
Arseneau et al.

(10) Patent No.: US 7,657,920 B2
(45) Date of Patent: Feb. 2, 2010

(54) SYSTEM AND METHODS FOR ENHANCING THE EXPERIENCE OF SPECTATORS ATTENDING A LIVE SPORTING EVENT, WITH GAMING CAPABILITY

(76) Inventors: Marc Arseneau, 16 St-Andrews, Morin Heights, Quebec (CA) J0R 1H0; Alain Charette, 328 des Eaux Vives, St-Jérome, quebec (CA) J7Y 4P1; Jean Arseneau, 480 De Bussy, Boisbriand, Quebec (CA) J7G 2J1; Michel Poisson, 5 Amance, Lorraine, Quebec (CA) J6Z 4N3

( * ) Notice: Subject to any disclaimer, the term of this patent is extended or adjusted under 35 U.S.C. 154(b) by 205 days.

(21) Appl. No.: 11/459,308

(22) Filed: Jul. 21, 2006

(65) Prior Publication Data
US 2007/0021058 A1    Jan. 25, 2007

Related U.S. Application Data

(60) Provisional application No. 60/701,473, filed on Jul. 22, 2005, provisional application No. 60/778,363, filed on Mar. 3, 2006, provisional application No. 60/789,911, filed on Apr. 7, 2006.

(51) Int. Cl.
*H04N 7/173* (2006.01)

(52) U.S. Cl. ..................................... 725/133

(58) Field of Classification Search .................. 725/22, 725/58, 62, 11–13, 16, 38, 42, 119, 129, 725/135, 139, 35, 133; 348/333.01, 468, 348/207.99; 370/350, 489; 473/407; 340/540
See application file for complete search history.

(56) References Cited

U.S. PATENT DOCUMENTS 4,139,860 A    2/1979    Micic et al.

(Continued)

FOREIGN PATENT DOCUMENTS

AU    779175    9/2000

(Continued)

OTHER PUBLICATIONS

Super Bowl XXXII Game Recap, www.nfl.com/superbowl/history/recap/sbxxxii, Jan. 26, 1998.

(Continued)

*Primary Examiner*—Joseph P Hirl
*Assistant Examiner*—An Nguyen
(74) *Attorney, Agent, or Firm*—Luis M. Ortiz; Kermit D. Lopez; Ortiz & Lopez, PLLC

(57) ABSTRACT

A handheld electronic device for use at a venue hosting a live sporting event, having a receiver for receiving a wireless RF transmission conveying a plurality of video streams derived from video cameras filming the live sporting event, a display and a user interface for selecting a video stream among the plurality of video streams to be displayed on the display. The handheld electronic device is capable to acquire a locked mode of operation and an unlocked mode of operation, in the locked mode of operation the handheld electronic device being precluded from displaying the video streams to a spectator, in the unlocked mode of operation the handheld electronic device being enabled to display the video streams to the spectator, the handheld electronic device capable to acquire the unlocked mode of operation in response to reception of authentication data wirelessly transmitted to the handheld electronic device.

9 Claims, 18 Drawing Sheets

U.S. PATENT DOCUMENTS

| | | | |
|---|---|---|---|
| 4,259,690 A | 3/1981 | Nakanishi et al. |
| 4,853,764 A | 8/1989 | Sutter |
| 4,866,515 A | 9/1989 | Tagawa et al. |
| 4,887,152 A | 12/1989 | Matsuzaki et al. |
| 5,003,300 A | 3/1991 | Wells |
| 5,012,350 A | 4/1991 | Streck et al. |
| 5,023,706 A | 6/1991 | Sandberg |
| 5,045,948 A | 9/1991 | Streck et al. |
| 5,047,860 A | 9/1991 | Rogalski |
| 5,068,733 A | 11/1991 | Bennett |
| 5,138,722 A | 8/1992 | Urella et al. |
| 5,161,250 A | 11/1992 | Ianna et al. |
| 5,189,562 A | 2/1993 | Greene |
| 5,289,272 A | 2/1994 | Rabowsky et al. |
| 5,392,158 A | 2/1995 | Tosaki |
| 5,434,590 A | 7/1995 | Dinwiddie, Jr. et al. |
| 5,485,504 A | 1/1996 | Ohnsorge |
| 5,504,535 A | 4/1996 | Abe |
| 5,510,828 A | 4/1996 | Lutterbach et al. |
| 5,513,384 A | 4/1996 | Brennan et al. |
| 5,539,465 A | 7/1996 | Xu et al. |
| 5,546,099 A | 8/1996 | Quint et al. |
| 5,574,964 A | 11/1996 | Hamlin |
| 5,598,208 A | 1/1997 | McClintock |
| 5,600,365 A | 2/1997 | Kondo et al. |
| 5,600,368 A | 2/1997 | Matthews, III |
| 5,617,331 A | 4/1997 | Wakai et al. |
| 5,664,880 A | 9/1997 | Johnson et al. |
| 5,666,151 A | 9/1997 | Kondo et al. |
| 5,696,521 A | 12/1997 | Robinson et al. |
| 5,708,961 A | 1/1998 | Hylton et al. |
| 5,729,471 A | 3/1998 | Jain et al. |
| 5,742,263 A | 4/1998 | Wang et al. |
| 5,793,413 A | 8/1998 | Hylton et al. |
| 5,797,809 A * | 8/1998 | Hyuga ........................ 473/407 |
| 5,806,005 A | 9/1998 | Hull et al. |
| 5,812,937 A | 9/1998 | Takahisa et al. |
| 5,815,216 A | 9/1998 | Suh |
| 5,847,771 A | 12/1998 | Cloutier et al. |
| 5,894,320 A | 4/1999 | Vancelette |
| 5,903,395 A | 5/1999 | Rallison et al. |
| 5,915,020 A | 6/1999 | Tilford et al. |
| 5,945,972 A | 8/1999 | Okumura et al. |
| 6,009,336 A | 12/1999 | Harris et al. |
| 6,020,851 A | 2/2000 | Busack |
| 6,078,874 A | 6/2000 | Piety et al. |
| 6,078,954 A | 6/2000 | Lakey et al. |
| 6,080,063 A | 6/2000 | Khosla |
| 6,097,441 A | 8/2000 | Allport |
| 6,100,925 A | 8/2000 | Rosser et al. |
| 6,124,862 A | 9/2000 | Boyken et al. |
| 6,125,259 A | 9/2000 | Perlman |
| 6,137,525 A | 10/2000 | Lee et al. |
| 6,182,084 B1 | 1/2001 | Cockrell et al. |
| 6,192,257 B1 | 2/2001 | Ray |
| 6,195,090 B1 | 2/2001 | Riggins, III |
| 6,271,752 B1 | 8/2001 | Vaios |
| 6,301,514 B1 | 10/2001 | Canada et al. |
| 6,351,252 B1 | 2/2002 | Atsumi et al. |
| 6,397,147 B1 | 5/2002 | Whitehead |
| 6,400,264 B1 | 6/2002 | Hsieh |
| 6,415,289 B1 | 7/2002 | Williams et al. |
| 6,424,369 B1 | 7/2002 | Adair et al. |
| 6,434,403 B1 | 8/2002 | Ausems et al. |
| 6,434,530 B1 | 8/2002 | Sloane et al. |
| 6,466,202 B1 | 10/2002 | Suso et al. |
| 6,469,663 B1 | 10/2002 | Whitehead et al. |
| 6,516,466 B1 * | 2/2003 | Jackson ........................ 725/62 |
| 6,522,352 B1 | 2/2003 | Strandwitz et al. |
| 6,525,762 B1 | 2/2003 | Mileski et al. |
| 6,526,335 B1 | 2/2003 | Treyz et al. |
| 6,526,575 B1 | 2/2003 | McCoy et al. |
| 6,535,493 B1 | 3/2003 | Lee et al. |
| 6,564,070 B1 | 5/2003 | Nagamine et al. |
| 6,570,889 B1 | 5/2003 | Stirling-Gallacher et al. |
| 6,578,203 B1 | 6/2003 | Anderson, Jr. et al. |
| 6,624,846 B1 | 9/2003 | Lassiter |
| 6,657,654 B2 | 12/2003 | Narayanaswami |
| 6,669,346 B2 | 12/2003 | Metcalf |
| 6,675,386 B1 | 1/2004 | Hendricks et al. |
| 6,681,398 B1 | 1/2004 | Verna |
| 6,782,102 B2 | 8/2004 | Blanchard et al. |
| 6,813,608 B1 | 11/2004 | Baranowski |
| 6,825,875 B1 * | 11/2004 | Strub et al. ............. 348/207.99 |
| 6,952,558 B2 | 10/2005 | Hardacker |
| 6,961,586 B2 | 11/2005 | Barbosa et al. |
| 6,965,937 B2 | 11/2005 | Gaddis et al. |
| 7,013,110 B1 | 3/2006 | Carpenter |
| 7,124,425 B1 | 10/2006 | Anderson, Jr. et al. |
| 7,149,549 B1 | 12/2006 | Ortiz et al. |
| 7,162,532 B2 | 1/2007 | Koehler et al. |
| 7,194,395 B2 | 3/2007 | Genovese |
| 7,210,160 B2 | 4/2007 | Anderson, Jr. et al. |
| 7,289,793 B2 | 10/2007 | Norwood |
| 2002/0042743 A1 | 4/2002 | Ortiz et al. |
| 2002/0057364 A1 | 5/2002 | Anderson, Jr. et al. |
| 2002/0058499 A1 | 5/2002 | Ortiz |
| 2002/0063799 A1 | 5/2002 | Ortiz et al. |
| 2002/0069419 A1 | 6/2002 | Raverdy et al. |
| 2002/0138587 A1 | 9/2002 | Koehler et al. |
| 2002/0152462 A1 | 10/2002 | Hoch et al. |
| 2002/0152476 A1 | 10/2002 | Anderson, Jr. et al. |
| 2002/0188943 A1 | 12/2002 | Freeman et al. |
| 2003/0007464 A1 | 1/2003 | Balani |
| 2003/0088873 A1 | 5/2003 | McCoy et al. |
| 2003/0112354 A1 * | 6/2003 | Ortiz et al. ............. 348/333.01 |
| 2003/0189668 A1 * | 10/2003 | Newnam et al. ............ 348/468 |
| 2004/0006774 A1 | 1/2004 | Anderson, Jr. et al. |
| 2004/0032495 A1 | 2/2004 | Ortiz |
| 2004/0073927 A1 * | 4/2004 | Knudson et al. ............... 725/58 |
| 2004/0136547 A1 | 7/2004 | Anderson, Jr. et al. |
| 2004/0158638 A1 | 8/2004 | Peters et al. |
| 2005/0028190 A1 * | 2/2005 | Rodriguez et al. ............ 725/22 |
| 2005/0201302 A1 | 9/2005 | Gaddis et al. |
| 2005/0210512 A1 | 9/2005 | Anderson, Jr. et al. |
| 2005/0216299 A1 | 9/2005 | Anderson et al. |
| 2005/0280705 A1 | 12/2005 | Anderson et al. |
| 2006/0174297 A1 | 8/2006 | Anderson, Jr. et al. |

FOREIGN PATENT DOCUMENTS

| | | |
|---|---|---|
| CA | 2237939 | 8/1998 |
| CA | 2369832 | 9/2000 |
| CA | 2 361 659 A1 | 5/2003 |
| EP | 0 578 201 A2 | 1/1994 |
| EP | 1166596 A1 | 1/2002 |
| GB | 2 355 135 A | 4/2001 |
| WO | WO 93/03571 A1 | 2/1993 |
| WO | WO 94/11855 A1 | 5/1994 |
| WO | WO 97/08896 A1 | 3/1997 |
| WO | WO 98/31148 A1 | 7/1998 |
| WO | WO 98/41020 A1 | 9/1998 |
| WO | WO 00/54554 A1 | 9/2000 |
| WO | WO 01/08417 A1 | 2/2001 |
| WO | WO 02/096097 A1 | 11/2002 |
| WO | WO 02/096104 A2 | 11/2002 |
| WO | WO 03/042939 A2 | 5/2003 |
| WO | WO 2004/034617 A1 | 4/2004 |
| WO | WO 2005/011254 A2 | 2/2005 |
| WO | WO 2005/076625 A1 | 8/2005 |
| WO | PCT/CA2006/001969 | 4/2006 |
| WO | WO 2006/065844 A1 | 8/2006 |

WO WO 2007/009225 A1 1/2007

OTHER PUBLICATIONS

Super Bowl XXXIII, Wikipedia, http://en.wikipedia.org/wiki/Super_Bowl_XXXIII, 1999.
Breier, Computer age comes to ballpark, North County Times, San Diego, Aug. 19, 1997.
Carter, Web Technology: It's in THE Game, www.microsoft.com/sitebuilder/features/superbowl.asp, Dec. 15, 1997.
ChoiceSeat™ Fact Sheet, Project: Super Bowl XXXII, Jan. 25, 1998.
ChoiceSeat™ Screen Shot, Superbowl XXXII, Jan. 25, 1998.
ChoiceSeat™ Advertisement, Pre-Super Bowl XXXII, Jan. 1998.
ChoiceSeat™ Advertisement, Pre-Super Bowl XXXII, Jan. 1998.
Fikes, For lucky 600 fans, there'll be TV sets at the seats, Super Bowl XXXII—It's just business, North County Times, San Diego, Jan. 14, 1998.
Stewart, Williams Interactive Video Gives Football Fans Choice, Tulsa World, Jan. 1998.
ChoiceSeat™ Hand Out at Super Bowl XXXIII, Jan. 25, 1998.
Just Call It Wired Bowl, Newsweek, Cyberscope, Jan. 28, 1998.
VYVX, Doctor Design, and Erbes Dev. Group Go to the Ball Game: Watch PC-TV, Internet TV at the Stadium, http://ruel.net/top/box.article.05.htm, Sep. 1, 1997.
Williams ChoiceSeat interactive network launches inaugural season with Tampa Bay Devil Rays; expands features for second season with San Diego Padres, www.williams.com/newsroom/news_releases/1998/rel175.htm, St. Petersburg and San Diego, Mar. 30, 1998.
ChoiceSeat Draft Requirements, Dec. 1998.
Super Bowl Turns Techno Bowl, The Herald, Jan. 24, 1999.
Williams Communications' ChoiceSeat™ demonstrates the interactive evolution of sports at Super Bowl™ XXXIII, www.williams.com/newsroom/news_releases/1999/rel287.htm, Tulsa, Jan. 20, 1999.
ChoiceSeat™ Advertisement, Pre-Super Bowl XXXIII, Jan. 1999.
ChoiceSeat™ Fact Sheet, Super Bowl XXXIII™, Pro Player Stadium, Miami, Florida, Jan. 31, 1999.
Super Bowl XXXIII Game Recap, www.nfl.com/superbowl/history/recap/sbxxxiii, Feb. 1, 1999.
CSI, Inc. (ChoiceSeat™) Business Plan, Aug. 1999.
ChoiceSeat™ User Guide, New York Knicks, Madison Square Garden, Aug. 1999.
ChoiceSeat™ User Guide, New York Rangers, Madison Square Garden, Aug. 1999.
ChoiceSeat™ Flowchart, New York Rangers, Madison Square Garden, Rev. 3.2, Nov. 16, 1999.
In-Seat Interactive Advertising Device Debuts, www.williams.com/newsroom/news_releases/1999/rel426.htm, New York, Nov. 19, 1999.
Intel and ChoiceSeat™ collaborate to advance interactive sports technology, www.williams.com/newsroom/news_releases/1999/rel429.htm, Santa Clara, Calif. and New York, Nov. 29, 1999.
Gordon, Interactive Broadband Video at the Garden, Digital Video Magazine, Apr. 2000.
Sweet, With Wired Seats, Fans Get Replays, Rules, Snacks, Wall Street Journal, May 21, 2000.
CSI Incorporated ("ChoiceSeat")—Executive Summary-Short Term Tactical Plan, May 2001.
Memorandum re Obviousness to Michele Connor and Craig Tyler, from Jean Theberge and Alain Charette, Nov. 2, 2007.
History of Wireless, Johns Hopkins School of Public Health, http://www.jhsph.edu/wireless/story.html, Nov. 12, 2007.
Wireless LAN, Wikipedia, Nov. 2007.
Carroll, Fans take to ChoiceSeats: Interactive technology, e-commerce expand to sporting events, Telephonyonline, Jan. 10, 2000.
Vela Research LP to Supply Encoding for ChoiceSeat at SuperBowl XXXII, St. Petersburg, FL, Jan. 13, 1998.
Stadium fans touch the future-Internet Explorer and touch screens add interactivity to Super Bowl XXXII, 1998.
San Diego Metropolitan Magazine, Jan. 29, 1998.
Grover, Armchair Baseball from the Web—or Your Stadium Seat, Business Week, Oct. 22, 1998.
Reality Check Studios Goes Broadband with Production for Choiceseat at Madison Square Garden, Hollywood, Calif., Dec. 1, 1999.
ChoiceSeat—Event Operations Manual for Madison Square Garden, 1999 Intel Corporation, Dec. 15, 1999.
ChoiceSeat screens, Jan. 1999.
ChoiceSeat—System Administrator's Binder for Madison Square Garden, Dec. 17, 1999.
ChoiceSeat™ Fact Sheet, Jun. 13, 2007.
ChoiceSeat Operations Manual: v.1.1, 1999.
ChoiceSeat Specification, Version 2.2, Williams Communications Group, Oct. 10, 1997.
Qualcomm Stadium, Choiceseat Network Diagram, May 11, 1998.
Proposed ChoiceSeat Client Specification Summary, Initial Draft Mar. 29, 1997, Updated Sep. 30, 1997.
Schedule of Personal Property, Patents, Software and Trademarks etc. Draft, CSI Incorporated, Aug. 28, 2001.
CSI Incorporated Draft—Schedule A-IP Intellectual Property, Aug. 28, 2001.
ChoiceSeat-The Premiere Provider of Interactive Event Entertainment, PowerPoint presentation, Jan. 2000.
ChoiceSeat Intellectual Property List, Aug. 28, 2001.
Proposed ChoiceSeat Network Specification Summary, Initial Draft, Aug. 25, 1997.
Proposed ChoiceSeat Network Specification Summary, Initial Draft Aug. 28, 1997; Updated Draft Aug. 28, 1997; Updated Draft Sep. 30, 1997.
Pocket Video Scanner 2.4 GHZ Band http://www.tetrascanner.com/pocket-video-scanner-details.html, Jul. 26, 2005, 1 page.
ICOM IC-R3 Receiver, http://javiation.co.uk/ic-r3.html, Copyright (c) Javiation 2000-2004, Jul. 26, 2005, 2 pages.
Video Signal Scanner: Wireless video scanner, Copyright 2003, http://www.spyequipmentguide.com/video-signal-scanner.html, Jul. 26, 2005, 1 page.
ICOM IC-R3—Meets MIL STD810, Communications Receiver, Copyright 2000 Icom Inc., 4 pages.
Federal Communications Commission, FCC OET Search Form, FCC ID = AFJIC-R3, https://gullfoss2.fcc.gov/cgi-bin/ws.exe/prod/oet/forms/reports/Search_Form.hts?mode=Ed..., 1 page.
Koyama, Takayoshi et al., ACM Press, International Conference on Computer Graphics and Interactive Techniques, Live 3D Video in Soccer Stadium, 2003, 2 pages.
Yan, Xin et al., ACM Press, International Multimedia Conference, 3D Reconstruction and Enrichment System for Broadcast Soccer Video, 2004, 3 pages.
Front Row Technologies, My Front Row (TM), Put the "Front Row" in the palm of you hand, http://www.myfrontrow.com/pages/439116/, Copyright 2001 by Mesa Digital LLC, 10 pages.
Slettenhaar, Henk et al., Silicon Valley Tour, Fall 2000, From Hollywood to Woodside, http://siliconvalley.ch, 38 pages.
Cadence Embedded Systems Design Services Brings the Scanz Scannor to Market, http://www.edacafe.com/technical/papers/Cadence/vol4No4/scanz.php, 1999 Cadence Design Systems Inc.
Macko, Steve, Security at the Summer Olympic Games is Ready, (c) Emergencynet News Service, 1996, Tuesday, Jul. 9, 1996, vol. 2—91.
Node, world leader in Location Based Media, nodeexplorer, http://www.nodeexplore.com/, Copyright Node 2005.
Office Action dated Aug. 20, 2008, U.S. Appl. No. 11/459,284, filed Jul. 21, 2006.
Response to Office Action dated Nov. 14, 2008, U.S. Appl. No. 11/459,284, filed Jul. 21, 2006.
Response to Office Action filed Aug. 21, 2009 in U.S. Appl. No. 11/459,284.
Office Action dated Feb. 23, 2009 in U.S. Appl. No. 11/459,284.

* cited by examiner

STANDINGS

| | | | | |
|---|---|---|---|---|
| 1 | BRUNO PELLETIER | ☐ 184 | 11 CHRIS BOLDUC | ☐ 55 |
| 2 | ORVILLE JORG | ☐ 164 | 12 FRANC GUAY | ☐ 45 |
| 3 | ADRIAN BOUCHER | ☐ 137 | 13 JIMMY REYMAND | ☐ 44 |
| 4 | HARVEY SIMS | ☐ 126 | 14 PIEIIR DELORME | ☐ 41 |
| 5 | CLARK BONG | ☐ 114 | 15 CHRISTIAN BERUBE | ☐ 21 |
| 6 | BOB OLIVER | ☐ 77 | 16 JEAN MARC | ☐ 20 |
| 7 | JIM DOMINGO | ☐ 76 | 17 TOM RAY | ☐ 12 |
| 8 | ALBERT MAN | ☐ 73 | 18 KELLY YUNG | ☐ 8 |
| 9 | DANIEL LONG | ☐ 73 | 19 DOMINIC JORDAN | ☐ 6 |
| 10 | KEVIN LARGE | ☐ 65 | 20 CAMERON TRACY | ☐ 4 |

↺ GO BACK          ⓘ MENU

FIG. 15

TEAMS   ☐

| | |
|---|---|
| TEAM 1 | TEAM 2 |
| TEAM DOE | PELLETIER RACING |
| TIM THOMPSON RACING | SPORTS RACING |
| YUNG RACING | TEAM JONG |
| JORDAN-TRACY RACING | DOMINGO / MAN RACING |
| DELORME COMPETITION | LARGE RACING |
| MI-JACK CONQUEST RACING | |
| GUAY/BOLDUC RACING | |
| PK RACING | |

↺ GO BACK     ◁◇▷ SELECT     👁 ENTER

FIG. 16

| TRACK | | TO GO | TIMING AND SCORING | | | |
|---|---|---|---|---|---|---|
| | | 4:70.81 | | | | |
| ST | NO | DRIVER | BEST LAP | LAG | PS | STA |
| 00 | | | 0.00:000 | 0.00:00 | 00 | |
| 02 | | | 4.55:'52 | 0.00:00 | 00 | |
| 00 | | | 0.00:000 | 0.00:00 | 00 | |
| 20 | | | 2.02:020 | 2.02:02 | 20 | |
| 20 | | | 2.02:020 | 2.02:02 | 20 | |
| 00 | | | 0.00:000 | 0.02:11 | 08 | |
| 00 | | | 0.00:000 | -.2':60 | 28 | @ |
| 00 | | | 0.00:000 | 0.00:00 | 00 | d |
| 00 | | | 0.00:000 | 0.00:00 | 00 | |
| 8 | | | .32:94 | 1.05:25 | 04 | ! |

↺ GO BACK    ⇕▷ SCROLL    👁 VIDEO

SYSTEM AND METHODS FOR ENHANCING THE EXPERIENCE OF SPECTATORS ATTENDING A LIVE SPORTING EVENT, WITH GAMING CAPABILITY

CROSS-REFERENCE TO RELATED APPLICATIONS

This application claims the benefit under 35 USC 119(e) of: U.S. Provisional Patent Application No. 60/701,473 filed on Jul. 22, 2005 by Jean Arseneau et al. and hereby incorporated by reference herein; U.S. Provisional Patent Application No. 60/778,363 filed on Mar. 3, 2006 by Jean Arseneau et al. and hereby incorporated by reference herein; and U.S. Provisional Patent Application No. 60/789,911 filed on Apr. 7, 2006 by Jean Arseneau and hereby incorporated by reference herein.

FIELD OF THE INVENTION

Broadly stated the invention relates to a system allowing wireless distribution of event-related video and/or audio content. The invention also extends to individual components of the system and associated methods of operation and use.

BACKGROUND OF THE INVENTION

The concept of delivering video and/or audio content to spectators attending a live sporting event is known. The typical approach uses a local transmission station that will deliver video and/or audio content over the air to handheld electronic devices operated by individual spectators. A spectator can select the particular video/audio stream of interest on the handheld electronic device.

SUMMARY OF THE INVENTION

As embodied and broadly described herein the invention provides a handheld electronic device for use at a venue hosting a live sporting event, comprising:
  a) a receiver for receiving a wireless RF transmission conveying:
    i) a plurality of video streams conveying live sporting event content, the live sporting event content including moving images of action occurring at the live sporting event held at the venue;
    ii) physiological data associated with a player involved in the live sporting event held at the venue.
  b) a display;
  c) a user interface for selecting a video stream among the plurality of video streams to be displayed on the display;
  d) the handheld electronic device capable of processing the physiological data for displaying physiological information associated with the player on the display.

As embodied and broadly described herein the invention provides a data structure embedded in a wireless RF transmission, the wireless RF transmission being intended for reception by a plurality of handheld electronic devices at a venue hosting a live sporting event, the data structure comprising:
  a) a plurality of video streams for display at handheld electronic devices, the plurality of video streams conveying live sporting event content, the live sporting event content including moving images of action occurring at the live sporting event held at the venue;
  b) physiological data associated with a player involved in the live sporting event held at the venue.

As embodied and broadly described herein the invention provides a handheld electronic device for use at a venue hosting a live sporting event, comprising:
  a) a receiver for receiving a wireless RF transmission conveying:
    i) a plurality of video streams conveying live sporting event content, the live sporting event content including moving images of action occurring at the live sporting event held at the venue;
    ii) video game data;
  b) a display;
  c) a user interface for selecting a video stream among the plurality of video streams to be displayed on the display;
  d) the handheld electronic device capable of processing the video game data for allowing the spectator to play a video game on the display.

As embodied and broadly described herein the invention provides a data structure embedded in a wireless RF transmission, the wireless RF transmission being intended for reception by a plurality of handheld electronic devices, the data structure comprising:
  a) a plurality of video streams for viewing at the handheld electronic devices, the plurality of video streams conveying live sporting event content, the live sporting event content including moving images of action occurring at the live sporting event held at the venue;
  b) video game data for execution by the handheld electronic devices allowing users of the handheld electronic devices to play a video game on displays of the respective handheld electronic devices.

As embodied and broadly described herein the invention provides a process for enhancing the experience of spectators attending a live sporting event held at a venue, the process comprising:
  a) producing while the live sporting event is ongoing a wireless RF transmission including a plurality of video streams conveying live sporting event content, the live sporting event content including moving images of action occurring at the live sporting event held at the venue, the wireless RF transmission being intended for reception by handheld electronic devices of respective spectators at the venue, each handheld electronic device:
    i) including a display allowing the respective spectator to view the video streams;
    ii) capable of game play function which allows a spectator to play a game on the handheld electronic device;
  b) conveying in the wireless RF transmission data for reception by the handheld electronic devices that enables the handheld electronic devices for game play function;
  c) controlling the conveying according to an evolution of the live sporting event, such that the handheld electronic devices are enabled for game play upon occurrence of one or more predetermined events during the live sporting event.

As embodied and broadly described herein the invention provides a handheld electronic device for use at a venue hosting a live golf game, comprising:
  a) a receiver for receiving a wireless RF transmission containing a plurality of video streams conveying different views of the golf game;
  b) a display;
  c) a user interface for selecting a video stream among the plurality of video streams to be displayed on the display;
  d) the wireless RF transmission conveying information on current weather at the venue, the handheld electronic device capable of communicating the information on current weather at the venue to the spectator.

BRIEF DESCRIPTION OF THE DRAWINGS

A detailed description of examples of implementation of the present invention is provided below with reference to the following drawings, in which:

FIGS. 7 to 18 are examples of screen views on the handheld electronic device illustrating typical information that can be delivered to the spectator;

Figure 1:
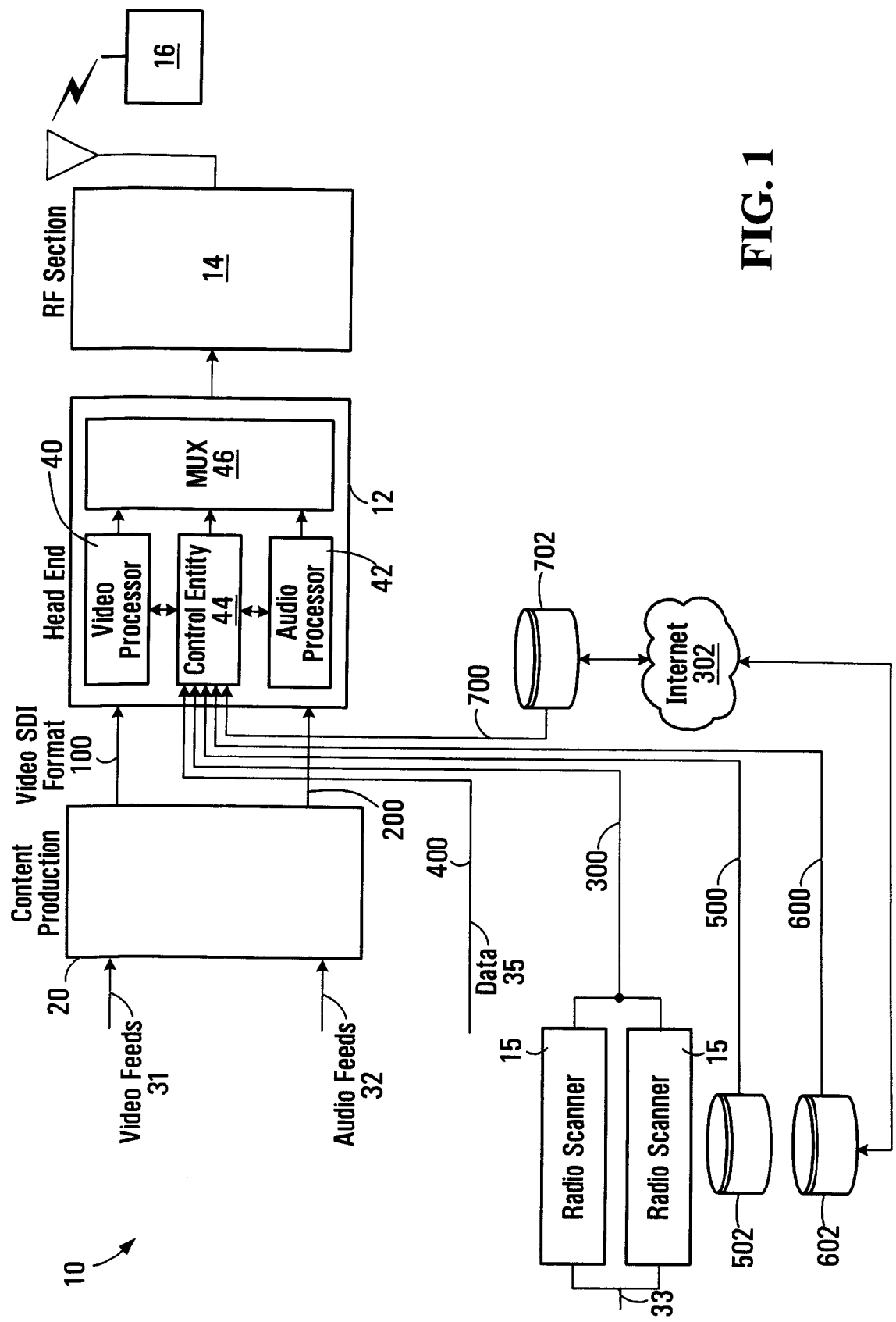
FIG. 1 is a block diagram of the overall system architecture.

In the drawings, embodiments of the invention are illustrated by way of example. It is to be expressly understood that the description and drawings are only for purposes of illustration and as an aid to understanding, and are not intended to define the limits of the invention.

DETAILED DESCRIPTION

FIG. 1 illustrates an overall system architecture, in accordance with a non-limiting example of implementation of the present invention. The system designated by the reference numeral 10 is intended to be used typically at a live sporting event. A live sporting event is a gathering of a large number of people, several hundreds or more, attending a public performance. Examples of live sporting events include but are not limited to:

A motor sport event, such as a car race, or motorcycle race;
A golf game;
A football game;
A soccer game
A baseball game
A hockey game;
A tennis game;
A horse race;
A polo game;
A basketball game;
The Olympic games The system 10 delivers to spectators attending the live sporting event video, audio and data content. For clarity, the invention can be used in connection with a wide variety of live sporting events without departing from the spirit of the invention. Accordingly, while the examples of implementation provided in this specification are made in connection with a car race, this should not be considered as a limiting feature.

As shown in FIG. 1, the system 10 includes a head end 12, a transmitter 14 and a number of handheld electronic devices 16, each electronic device 16 being intended to be used by a single spectator. While a single electronic device 16 is shown, in most practical applications almost any number of handheld electronic devices 16 can be accommodated. For instance, in a car race that may attract several tens of thousands of attendees, the head end 12 and the transmitter 14 can support an equal number of handheld electronic devices 16.

The transmitter 14 communicates with the individual handheld electronic devices 16 in a wireless manner. In the example that is being shown in the drawings, the communication is a Radio Frequency (RF) communication. This RF transmission is unidirectional. In other words, the information flow is from the transmitter 14 to each electronic device 16. This is accomplished in the broadcast mode wherein each electronic device 16 receives the same information from the transmitter 14. In the unidirectional RF transmission, the handheld electronic devices 16 are unable to transmit information back to the transmitter 14 over the wireless RF communication link.

In a non-limiting example of implementation the wireless RF transmission is performed locally of the venue. "Locally of the venue" means that the antenna generating the wireless RF transmission originates either at the venue or outside the venue but generally close to the venue. The signal power level is also controlled such that handheld electronic receivers 16 can adequately receive the wireless RF transmission at the venue, but at significant distances from the venue the signal weakens and may no longer permit a quality reception. By "significant" distance is meant a distance in terms of kilometer range.

It should be understood that the handheld electronic devices 16 are capable of unidirectional wireless communication, as described above, or alternatively, they can be capable of bidirectional wireless communication. In the case of unidirectional wireless communication, the handheld electronic devices 16 are only able to receive wireless information. In other words, they are not able to transmit information back to the transmitter 14, or to another entity, over a wireless communication link. It should be appreciated that although the handheld electronic devices 16 may only be capable of unidirectional wireless communication, they may be operative to transmit and receive information over a wireline link, such as via a USB connection port, for example.

In the case of bidirectional wireless communication, each electronic device 16 is able to receive information over a wireless communication link, and is also able to transmit information over a wireless communication link. In this case the electronic device 16 is provided with an RF transceiver (not shown in the drawings) that can handle the receive and transmit functions. The transmitted information may be sent to an entity of the system 10 (not shown), or to an entity that belongs to an external network. The handheld electronic devices 16 may be operable to transmit information over a wireless RF communication link, such as over a cellular link. In the case of a cellular link, the handheld electronic devices 16 would dial a phone number and then transmit information to the receiver/transceiver over the cellular link. Certain situations in which it may be preferable for the handheld electronic devices 16 to have bidirectional wireless communication capability will be described in more detail further on in the specification.

The bi-directional communication feature may be implemented to provide identical or similar bandwidths over the receive and transmit links. However, in most cases, this is not necessary since the amount of information that needs to be sent from the handheld electronic device 16 is generally different from the amount of information that it needs to receive. Typically, the handheld electronic device 16 needs to send far less information than that it receives. The implementation using the cellular network is an example that would provide a sufficient bandwidth over the transmit link. By "cellular" network is meant a network that uses a series of cells having a limited geographical extent within which communication services are available. In one possible form of implementation, such cells can be arranged to provide a hand-off to moving handheld electronic devices 16, such that as a handheld electronic device 16 moving outside a cell and entering a new cell, the communication services as seamlessly transferred from one cell infrastructure to another cell infrastructure. The "cellular" network terminology encompasses both communication infrastructures using licensed bandwidth, such as typical cellular telephones based on Code Division Multiple Access (CDMA), Time Division Multiple Access (TDMA), Groupe Station Mobile (GSM), or other technologies, and communication infrastructures using unlicensed bandwidth, such as Wireless Fidelity (WiFi) that is used commonly to provide wireless access to computer networks. Another possible example of a "cellular" technology using unlicensed bandwidth is the so called "Bluetooth" protocol that provides very short range wireless communication capabilities.

The cellular link allows the electronic device 16 to transmit information over a relatively limited bandwidth, however, in most cases the amount of information that needs to be sent is low such the available bandwidth should suffice. On the other hand, the receive link has a higher bandwidth in order to accommodate the multiple video streams and the other data that is to be sent to the electronic device 16. Also the cellular link allows the handheld electronic devices 16 to transmit information independently from one another.

The head end 12 receives content that originates from various sources. The content can be formatted or edited before being input into the head end 12. In the example shown in FIG. 1, a number of content sources are shown, which for the purposes of the present application will be described in the context of a car race. There are multiple video feeds 31 that originate from cameras along the racetrack or at locations adjacent to the racetrack such as the pits. The cameras capture images of the live sporting event and output the video information making up the respective video feeds. Multiple audio feeds 32 are also provided, where each audio feed 32 is associated with a video feed 31. An audio feed 32 conveys audio information such as the noise picked up by a microphone at a location at which the associated camera is placed, or an audio commentary. Such audio commentary can be the speech picked up by a microphone from a commentator or any individual that appears in one or more of the video feeds. Independent audio feeds 32 are also provided that convey independent audio content which is not associated with any particular video content. For instance those independent audio feeds 32 may be radio conversations between drivers and the pit crew. Such audio conversations are picked up by an array of radio scanners 15 each tuned to a particular frequency allocated to a given race team.

The audio and video data is typically supplied by the authority managing the live sporting event. For example, in the case of a car race, the video and audio data might be supplied by the National Association for Stock Car Racing (NASCAR). In a further non-limiting example, the independent audio feeds that contain audio commentary may be supplied by the commentator's affiliated television network, such as TSN, for example.

The content sources also include real time data content 35. The real time data content 35 conveys information relating to the action the spectator sees. For example, the real time data content in the context of motor sports, such as a car race, can be time and ranking information, lap times, position of the various cars on the track, physiological information about a driver, among many others. The real time data content is typically also supplied by the authority managing the live sporting event.

The video feeds 31 and the audio feeds 32 (except the independent audio feeds) are edited at a content production station 20. The content production station 20 is not part of the system and it merely provides a facility where a technician can format or edit the raw content to make it more suitable for presentation to the audience. The content production station 20 includes a console that allows the technician to conduct the necessary content editing operations. The content production station 20 does not form part of the invention.

In the embodiment shown in FIG. 1, the head end 12 receives seven different inputs. Those inputs are broadly described below:

1. The first input, designated by reference numeral 100 includes the multiple edited video feeds that are transmitted according to a Serial Digital Interface (SDI) format.
2. The second input 200 includes the multiple edited audio feeds 32 that are associated with respective video feeds 31. Those audio feeds 32 are transmitted in analog format. For instance, each audio feed 32 may be sent in a separate frequency band.
3. The third input 300 includes the independent audio feeds 33, which are also transmitted in analog format sent over independent frequency bands. As indicated earlier, an independent audio feed 33 may convey voice conversations, audio commentaries, etc . . . , picked up by a radio scanner 15.
4. The fourth input 400 includes the real time data content 35 that is transmitted digitally to the head end 12. In one non-limiting example, the real-time data content includes information relating to the live sporting event, such as for example scoring and participant ranking information, among others. In the specific example of a car racing event, the real-time information can include:
   the current ranking;
   number of laps remaining;
   participants still in the race;
   participants no longer in the race;
   fastest lap of the current leader or of anyone of the participants;
   average speed of the current leader or of anyone of the participants, among others;
   present speed of any one of the participants;
   Revolutions Per Minute (RPM) of the engine of anyone of the participants;
   The engaged gear in the transmission of any one of the participants;
   In another example, the real-time data content can also convey physiological information associated with anyone of the participants. Again in the context of a car race, the physiological information can include the heart rate of the driver or his body temperature, among others. The real time data content is usually available from the authority sanctioning the live sporting event. In the case of the physiological information, one possible implementation would require providing one or more of the participants with the necessary sensors that measure the heart rate, body temperature, etc and convey the collected information to the head end 12 such that it can be included in the wireless RF transmission. It is not deemed necessary to describe in detail how the physiological information is collected and delivered to the head end 12, since this would be known to a person skilled in the art.

5. The fifth input 500 includes authentication data received from an authentication database 502. The authentication data 500 is digitally transmitted to the head end 12.

6. The sixth input 600 includes ancillary content that is output from an ancillary information database 602. The ancillary content 600 can be in the form of video, audio or data, such as text for display to the spectator. Examples of ancillary content includes:

a) Advertisement content. The advertisement content can be delivered in the form of video, audio or a combination of video and audio. Examples include short movies, still images, or portions of still images appearing as overlays on other video content appearing on the spectator's screen. The advertisement content can be delivered in a wide variety of ways. Examples include:

(1) A first possibility is to broadcast the advertisement content such that it is played at each electronic device 16. In this fashion each spectator is exposed to the same content. Ads can be channeled to the handheld electronic devices 16 over individual video/audio streams such that the spectator can select when to view the ads or not view the ads. For example, the electronic device 16 can be programmed in a way to allow the spectator to access a special add channel that continuously runs the ads content. Alternatively, ads can be inserted in the video/audio streams that convey the event-related content. The insertion of the ads can be done upon occurrence of one or more predetermined events during the game. For example, during idle times, ads can be run. Such ads can be in the form of short movies that are played on the electronic device 16 for a predetermined time period, such as 30 seconds. Another possibility is to present the ads as banners, logos or in a "ticker" type fashion that appears on certain areas of the screen of the handheld electronic device 16.

(2) A second possibility is to deliver the ad content according to spectator profiles. The ads are organized into blocks, where each block corresponds to a spectator profile. Spectator profiles can be defined in various ways, such as age groups, gender, level of revenue, area of interest or combinations of the above, among many others. For instance, with profiles that are distinguished from one another on the basis of gender, ads that are intended to attract the interest of males can be directed in one profile while ads that are more likely to be of interest to females can be placed in the other profile. In the case of profiles that are distinguished on the basis of revenue level, ads on products or services would be placed in profiles according to the cost of the product or service; more expensive products or services would be placed in profiles associated with higher revenue levels.

b) Venue or event related contextual content. In the case of motor sports, such as car races, the contextual content may include information about the track or venue, such as:
   a map of the track and/or of the venue
   the history of the track and/or venue;
   the list of the racing teams;
   the information about each team;
   information about the drivers and cars;
   instructions on where to find certain facilities at the venue such as washrooms, vending machines or stands, among many others.

c) News. The news content may include "breaking" news bulletins, weather information, and economic information such as stock exchange averages or indices, among others.

d) Environmental conditions. In the case of certain events, such as golf games, environmental conditions can greatly affect the way the game is played. As such, information relating to environmental conditions such as:
   current temperature;
   wind speed;
   wind direction;
   humidity;
   weather forecast.

e) Shopping Information. A shopping service may be provided to a spectator in order to enable the spectator to purchase products or services related to the live sporting event, such as T-shirts, caps, related sporting equipment and autographed items from the players or participants. The shopping information may be displayed in the form of an electronic catalogue of purchasable items that lists the products and paraphernalia that are for sale. The shopping catalogue may also include products from the sponsors of the sporting event.

In a non-limiting example of implementation, the advertisement information described above in paragraph a) may be tied into the shopping service. For example, during the sporting event, the advertisement information may indicate to a spectator that products from the event's sponsors are available for purchase in the shopping catalogue. In addition, when an exciting event occurs in the live sporting event, such as a winner of the event is determined the advertisement information can indicate to a spectator that T-shirts and other items associated with the winner of the event can be bought via the shopping catalogue.

In order to purchase products from the shopping catalogue, a spectator would add selected items to a virtual "shopping cart" and then "checkout".

In the case where the electronic device 16 is only capable of unidirectional wireless communication, the spectator would then have to physically connect the electronic device 16 (via a USB port, for example) to a purchasing terminal located at the sporting event, or to their PC when they arrive home. The purchasing information would then be downloaded from the electronic device 16 to the terminal or PC, which can then transmit the information to the appropriate entity.

Alternatively, in the case where the electronic device 16 is capable of bidirectional wireless communication, as described above, the purchasing information can be sent immediately over a wirelessly communication link, to an appropriate receiver/transmitter to complete the on-line purchase. The appropriate receiver/transmitter may be part of the system 10, or may be part of an external network.

f) Trivia games and/or Surveys. During the course of a live sporting event, the handheld electronic device 16 can present to the spectator a series of questions in the form of either a trivia game or a survey. This could be done either to gather information from the spectator or to entertain the spectator during the idle time of the live sporting event. The spectator would be able to respond to the questions, which may be in yes/no format, or multiple choice format, via a user interface of the electronic device 16.

In the case where the electronic device 16 is only capable of unidirectional wireless communication, the spectator would physically connect the device (via a USB port, for example) to a terminal located at the live sporting event, or to a PC when they arrive home, in order to transmit their answers to an external device. This information can then be transmitted to the appropriate entity. In the case where the questions are in the form of a trivia game, by submitting the spectator's answers to the game, the spectator may be eligible to win a prize.

Alternatively, in the case where the device is capable of bidirectional wireless communication, as described above, the answers to the trivia or survey questions can be sent via a wireless communication link, such as a wireless RF link (for example a cellular link) directly to an entity that is monitoring the results. Ideally, in the case of a trivia game scenario, numerous spectators at the live sporting event could respond to the questions in real time, such that the results could be compiled and conveyed to the crowd almost immediately. The excitement created by a real-time trivial game, that awarded prizes to participants, could help to enhance the spectators' enjoyment of the live sporting event. The trivia/survey can be conditioned on the way the live sporting event unfolds. For instance, the trivia is designed such as to produce questions in connection with the participant that leads the race. Generally, the service data that is sent periodically to the handheld electronic devices 16 would include the information allowing each handheld electronic device 16 to display question and answer choices. The answer by the spectator can be collected as described earlier. Another option is to send along with the trivia/survey questions the answers such that the spectator can see if he or she has provided the correct response to the question. In this case the trivia/survey is provided for enjoyment by the spectator, without any centralized collection of the answers.

7. Finally, the seventh input 700 includes service data. The service data resides in a database 702. This database can also connect to the Internet to obtain updates or program releases that may not be available prior the beginning of the event being serviced by the system 10. Examples of service data include:

a) Data for setting the software running each electronic device 16 (For the purpose of this specification "setting" means either altering the software that may already be in the electronic device 16 or loading new software that was not present in the electronic device 16). For example, the service data may be used to upload an entirely new or portions of a Graphical User Interface (GUI) to the handheld electronic devices 16 in order to customize the handheld electronic devices 16 for the event. One example of a portion of a GUI that can upload is data that forms a menu on the electronic device 16. The menu is such as to provide the spectator with a list of options. Another GUI element can be graphical information that can be tailored to the event, such as background images on which other GUI elements can be displayed to the spectator. The service data may upload the Graphical User Interface (GUI) in multiple different languages so as to provide multiple language support to the spectators using the handheld electronic devices 16. In this manner, spectators using the handheld electronic devices 16 can select their language of preference. The choice of language may be presented to the spectators in an initial start-up screen that is displayed upon powering up the electronic device 16. Specifically, the following components of the user interface can be set via the service data:

i) Background image information;
   As discussed above this is the graphical information associated with the user interface.
ii) Menu structure and look;
   This refers to the option items of the menu, in particular the options hierarchy, the options themselves (what are the options available to the spectator from which the spectator can select an action), the graphical elements of the menu, such as the disposition of the option items on the display, color and shape of the option items, etc.
iii) Soft keys layout and look (soft keys will be discussed later);
   The aesthetical components of soft keys, such as their location on the screen, their shape, color, etc.
iv) Soft keys assignments;
   The functions assigned to the respective soft keys
v) Layout of icons on the display;
   The appearance and disposition of the icons on the display screen
vi) Navigation mechanisms
   The type of navigation mechanisms to which the user interface responds, such as up, down, left and right arrows, pointing devices, voice recognition, etc.

b) Cartographic data that can be used by the electronic device 16 to display a map of the venue or a portion thereof. The cartographic data can be used as in a standalone manner to show on the display of the handheld electronic device 16 a map of the venue that can be zoomed in or out to the desired degree of detail or panned to show different areas of the map. Alternatively, the cartographic data can be used in conjunction with a coordinates receiver, such as a Global Positioning System (GPS) receiver that can generate the coordinates of the location of the electronic device 16. The coordinates can then be used to show on the display the map of the venue and point the location of the electronic device 16. The cartographic data can also include specific locations of interest such as washrooms, vending stands, parking, etc. When the cartographic data is intended to work with location information generated by a GPS receiver or any other suitable device capable of producing location information it will typically be georeferenced. For maps that are not intended to work with devices producing location information, such georeferencing is not required since the map is processed simply as an image to be viewed by the spectator.

c) Video game data for allowing the spectators at the individual handheld electronic devices 16 to play one or more video games. The video game data contains program code for execution by the processor of the electronic device 16 to enable the spectator to play a video game on the display of the handheld electronic device 16. The video game that is used for the entertainment of the spectator has images that can be manipulated on the display. The video game is controlled via the user interface.

The ancillary content 600 can be obtained from a wide variety of sources. The advertisement, shopping, venue or event related information can be recorded on any suitable medium and injected in the video/audio content at the head end 12. Specifically, the advertisement, shopping, venue or event related information could be digitally stored on a database 602. The output of the database 602 leads to the head end 12 such that the video/audio content in the database 602 can be injected in the video/audio content that is being broadcast to the handheld electronic devices 16. The Internet is another source of ancillary content. Specifically, the news service can be delivered from the internet and injected in the video/audio content that is being broadcast to the handheld electronic devices 16.

Figure 2:
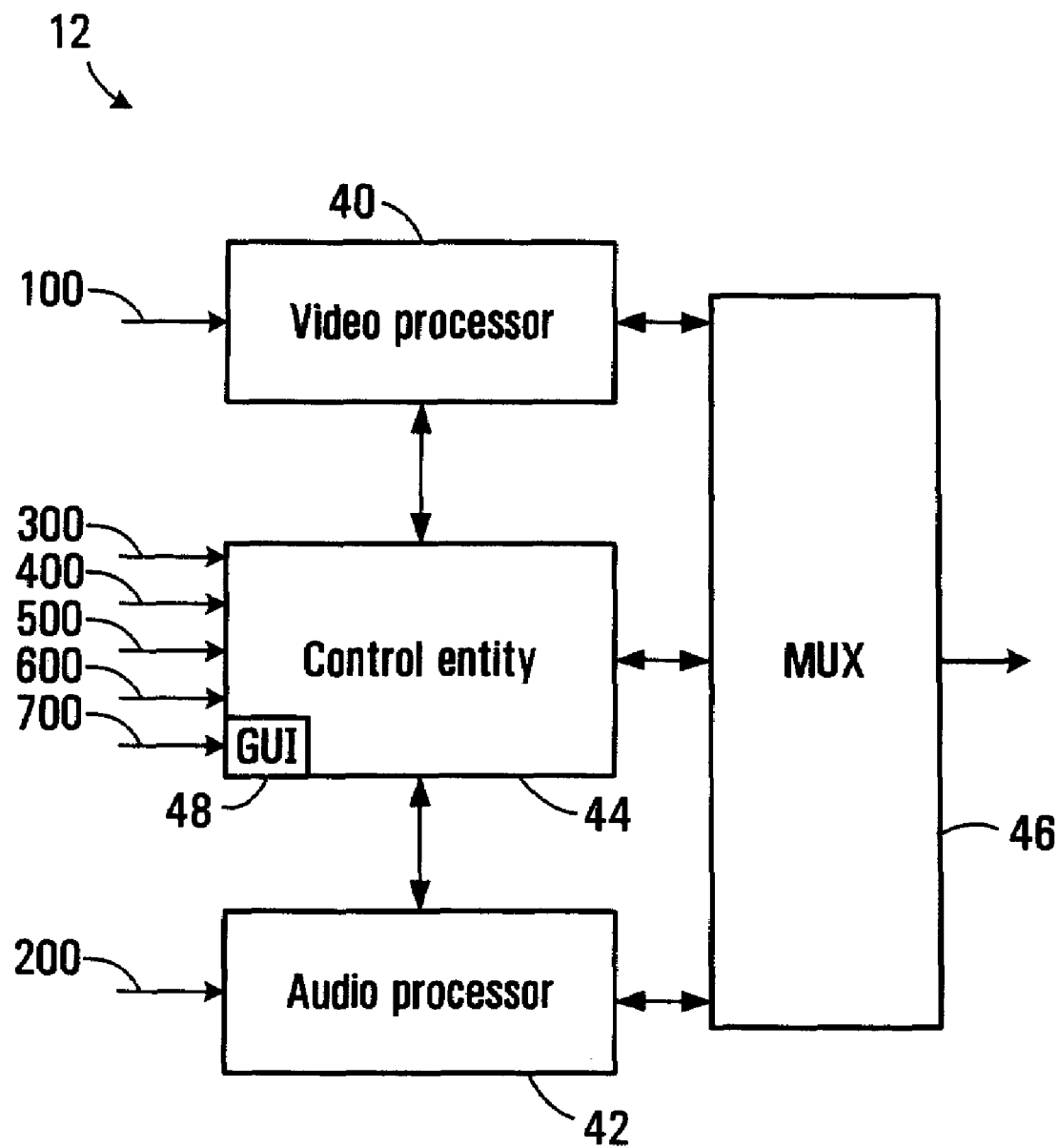
FIG. 2 is a detailed block diagram of a head end.

FIG. 2 shows a more detailed block diagram of the head end 12. The head end 12 organizes the data from the various inputs into a structured information stream for broadcasting to the individual handheld electronic devices 16. The head end 12 has a video processor 40, an audio processor 42, a control entity 44 and a multiplexer 46. The control entity 44 includes a computing platform running a program to carry out various tasks. While not shown in the drawings, the computing platform includes a processor, memory to hold the program code and data that is being processed by the processor. In addition, the computing platform has a Graphical User Interface (GUI) 48 that provides a technician with the ability to send commands to the control entity 44 or to receive information therefrom. The GUI 48 can take various forms without departing from the spirit of the invention. For instance, the GUI 48 can include a display on which information is shown to the technician and a keyboard and mouse combination for data and commands entry.

The control entity 44 receives the various forms of information and will direct them to the appropriate encoders for processing. Specifically, all the video feeds that are received at the first input of the control entity 44 are switched to a video processor 40 that will convert the SDI format into Moving Picture Experts Group (MPEG)-4 format. Each video stream is compressed to provide at the handheld electronic device a moving image at 30 Frames per second (fps), 16 bit colors at a 320×240 pixels resolution. The resulting bit rate is 384 Kbits/sec.

Since the video processor 40 needs to handle multiple video feeds simultaneously it is designed in order to be able to process those feeds in parallel. The preferred form of implementation uses a plurality of encoder stations, each being assigned a video feed 31. The encoder stations can be based on dedicated video processing chips or purely on software, or a combination of both. Alternatively, the video processor 40 can use a single processing module with buffering capabilities to sequentially handle blocks of data from different video feeds 31. With an adequate size buffer and a processing module that is fast enough, all the video feeds 31 can be encoded without causing loss of data.

In a non-limiting example of implementation, the encoder stations of the video processor 40 are operative to encode "bookmarks" data into the video feeds. The "bookmarks" data acts as pointers to specific portions of the video feed. Generally, these pointers are included to mark portions of the video feed that might be of interest to a spectator of the electronic device 16 to view.

For example, if the live sporting event is a car race, and one of the video feeds includes footage of a car crash, the encoder that is formatting that video feed 31 may include a "bookmark" data that points to the location in the video feed where the car crash commenced. As such, when the video feed is sent to the electronic device 16, the spectator is informed that there is a bookmark associated with the car crash, and by selecting the bookmark, the electronic device 16 plays the video feed starting at the portion pointed to by the "bookmark" data. As such, the electronic device 16 will display the specific portions of the video that relate to the car crash. This feature is particularly useful when the electronic device 16 has video playback capabilities, hence the spectator can play back the video content and use the bookmarks as reference to find events of interest. Other examples where a bookmark may be used include a football event. Bookmark data can be placed in the video feed when a touchdown occurs, such that the spectator can easily locate the salient parts of the game. The decision to place bookmark data in a video feed is taken by the individual that manages the head end 12 or any other person that has content editing responsibilities. The bookmark data is generated by the head end 12, in response to input from the operator on the user interface 48. The use of "bookmarks" will be described in more detail further on in the description.

Note that since MPEG-4 encoding also handles audio, the audio feeds 32 that are associated with the respective video feeds 31 are also directed to the video processor 40. The output of the video processor 40 is thus MPEG-4 encoded video channels where each channel has a video stream portion and an audio stream portion.

The independent audio feeds 33 that are received at the third input 300 are directed to an audio processor 42 that will encode them into a Moving Pictures Experts Group Audio layer 3 (MP3) format. Since the MP3 encoded video feed 31 convey voice information they can be compressed into an 8 Kbits/sec data rate while maintaining adequate quality. As in the case with the video processor 40, the audio processor 42 uses a series of audio encoding stations, each dedicated to a given audio feed (from the second input and the third input). Alternatively, the audio processor 42 can use a single sufficiently fast encoding module having buffering capabilities to sequentially handle data blocks from all the audio feeds 32.

As will be described in more detail further on in the specification, the encoding stations can encode each audio feed such that the transmitter 14 and/or the handheld electronic devices 16 can detect based on the encoding whether the feed is active or inactive. An active audio stream is an audio stream that conveys some type of information the spectator can understand. In contrast, an inactive audio stream is a stream that that conveys no such information, such as low intensity noise, for example silence. Specifically, the encoding station can be provided with logic that detects the level of activity in the signal in an attempt to recognize if the signal carries active speech or sounds or simply low intensity noise. The logic rules allowing to discriminate between active audio and silence are generally well known and do not need to be described in detail. One specific possibility is to monitor the signal level or the degree of energy conveyed by the signal and use a threshold as a decision making point. Anything below the threshold is considered to be low intensity noise, such as silence while everyting above is active audio information, such as speech. The condition of the audio stream, in other words either silence or active audio information can be communicated to the handheld electronic device 16 by inserting a flag or any other type of mark in the binary stream wirelessly broadcast to the handheld electronic devices 16. In the case of a flag, one binary value means silence while the other binary value means active speech. In addition to making a determination on the condition of the audio stream, the condition that is observed can be used to simply stop the encoding process when silence is encountered and subsequently resume the encoding process when active speech is produced.

The control entity 44 handles the processing of the fourth, fifth, sixth and seventh inputs, namely the real time data, the authentication data, the ancillary content and the service data. The purpose of the processing is to packetize the data such that it can be transmitted to the individual handheld electronic devices 16.

The outputs of the control entity 44 and the video and the audio processors 40 and 42, are passed to a multiplexer 46 that combines the data into one common data stream. The data stream is then directed to a transmitter 14 that produces a wireless RF transmission broadcasting the information to the individual handheld electronic devices 16. The transmitter 14 can be designed to use a single 6 MHz contiguous channel bandwidth to broadcast the entire payload to the handheld electronic devices 16. The table below provides an example of a payload.

| Description | Required unit bit rate | Number of feeds | Aggregated bit rate |
|---|---|---|---|
| Live video feeds 31, 320 × 240 pixels, 16 bit colors, 30 Fps (Mpeg 4) | 384 Kbits/s each | 10 | 3.84 Mbits/s |
| Audio feeds 32 (synchronized with video feeds-MP3) | 28.8 Kbits/s each | 10 | 288 Kbits/sec. |
| Independent voice grade compressed audio feeds 33 (MP3) | 8 Kbits/sec. each | 48 | 384 Kbits/sec. |
| Real time data 35–6,000 ASCII Characters (or equivalent data payload) of high priority refresh | 480 Kbits/s each | 1 | 480 Kbits/sec. |
| Ancillary content and service data, (several priority refresh levels) | 1 Mbits/s | 1 | 1 Mbits/sec. |
| Authentication data | 256 bits/ 30 sec. | 50,000 | 425 Kbits/sec. |
| Spare | | | ≈1 Mbits/sec. |
| Overall payload | | | 7.5 Mbits |

The data stream that is being broadcast from the transmitter 14 to the individual handheld electronic devices 16 is organized in the form of digital packets. In a specific and non-limiting example of implementation, three types of packets are being sent. The first type includes the video information. In essence, the MPEG-4 information stream is packetized and transmitted. The video information packet includes a header that contains the relevant data allowing the electronic device 16 to appropriately decode it and process it. Advantageously, error detection and correction data is also included in the header for a more reliable transmission. The second type of packet includes the independent audio information. The third type of packet includes the remainder of the payload, such as the ancillary information and the real and service type data. As in the case of the first type of packet, the second and third types of packets include identification data in the header to inform the handheld electronic device 16 what type of content the packet holds such that the content can be adequately processed.

Figure 3:
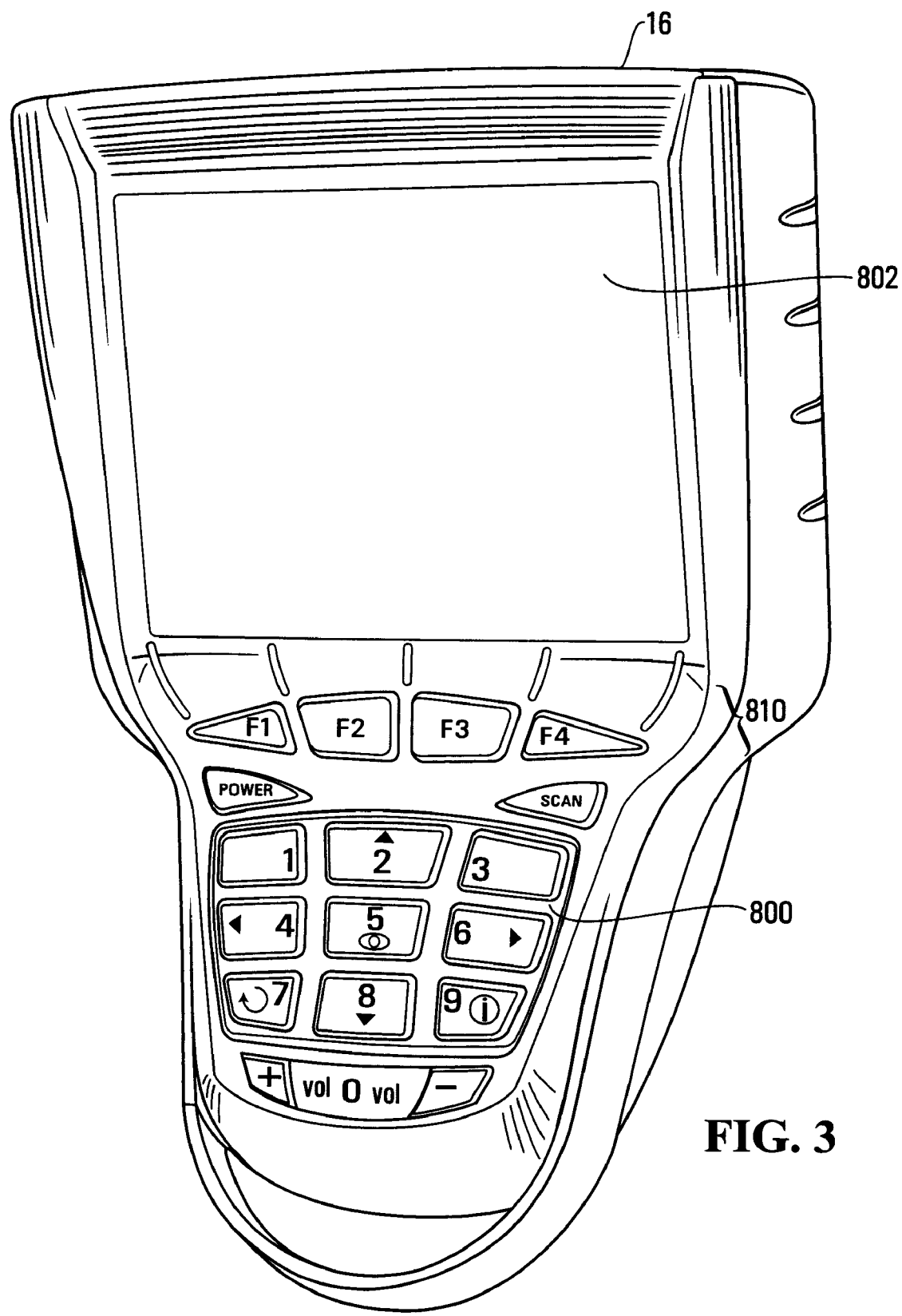
FIG. 3 is a perspective view of a handheld electronic device.

FIG. 3 shows a perspective view of the electronic device 16. The electronic device 16 is a hand-held device designed to fit comfortably in the spectator's hand. It includes a keyboard 800 with the necessary keys to control the operation of the electronic device 16. Above the keyboard 800 is provided a display section in which is placed a display screen 802.

Figure 4:
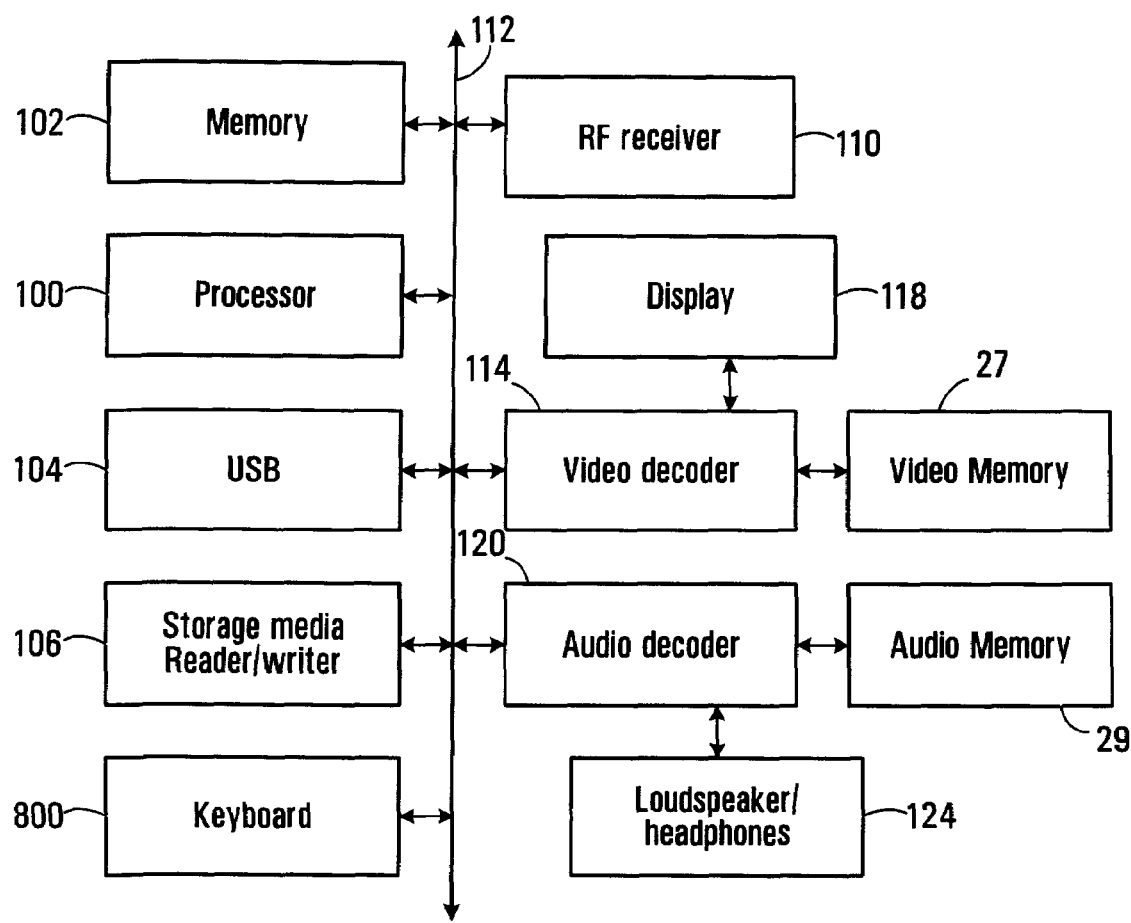
FIG. 4 is a block diagram of the handheld electronic device.

FIG. 4 is a block diagram of the electronic device 16. The electronic device 16 is a computer-based device that receives the information sent by the transmitter 14. The video information is displayed on the display screen 802 and the audio information is played via suitable speaker/headphones 124. The spectator can control the selection of the video channels as well as to perform other operations. By video channel at the electronic device 16, it is meant a combination video stream and an associated audio stream.

As seen in FIG. 4, the electronic device 16 has a processor 100 that executes software for controlling the various functions of the electronic device 16. Generally, the software has four main layers, namely:

The configuration layer

The configuration layer allows the spectator or the manufacturer to set characteristics of the electronic device 16, such as enable or disable options, language, time, passwords, etc.

The GUI layer

In the example described in this specification the GUI includes a graphical and navigation layer that allows the spectator to access specific functions of the electronic device 16. The GUI would typically present to the spectator on the screen options, such as menus that the spectator can navigate to access the feature that is desired. As indicated earlier, the service data portion of the payload broadcasted by the transmitter 14 contains information that defines how the graphical and navigation layer will appear to the spectator. The following are examples of the types of information the service data portion can convey as it pertains to the GUI in order to set the GUI for use:

i. Background image—an image that appears on the screen and on which are overlaid other types of information such as menu choices. For instance the background can have a visual theme associated with the event or venue. The background image can change for different events or venues;

ii. Menu choices—define the options hierarchy that is available to the spectator. For example, for a certain event, 10 video channels are available but for other events, fewer or more channels are possible.

iii. Menu look and details—the visual appearance and prompts associated with the various menu choices. For instance, the different video channels may have names or identifiers associated therewith, such as the video channel at the pits, the video channel from the camera inside the race car of driver XYZ or the video channel from the left corner of the racetrack.

iv. Soft keys assignment—Referring briefly to FIG. 3, the handheld electronic device is provided with Function keys 810 (F1, F2, F3 and F4). The user interface may assign to different functions to each physical key F1, F2, F3 or F4. In a specific and non-limiting example of implementation, the current assignment of a key is displayed on the display 802, immediately above the associated physical key (F1, F2, F3 or F4).

v. Soft keys layout and look—The aesthetical components of soft keys, such as their location on the screen, their shape, color, etc.

vi. Layout of icons on the display—The appearance and disposition of the icons on the display screen.

vii. Navigation mechanisms—The type of navigation mechanisms to which the user interface responds, such as up, down, left and right arrows, pointing devices, voice recognition, etc.

In a non-limiting example of implementation, the data for setting the GUI in the electronic device 16 is sent wirelessly from the transmitter 14 that is used to send the wireless RF transmission conveying the payload. In one possible example, the data for effecting the GUI setting is sent during a window of operation that precedes the beginning of the transmission of the video streams. For instance, in the context of motor sports, such as a car race, this can be done before the race event starts. In a second example, the data for setting the GUI is sent along the other payload. As far as the electronic device 16 is concerned, after the data for configuring the GUI is received it is loaded such that the spectator will be presented with the new GUI. When an authentication process is required to allow the electronic device 16 to access the video streams, as will be described later, the actual loading of the new GUI can be deferred until the authentication has been completed.

The baseline code

In a specific and non-limiting example of implementation, a LINUX kernel is used to provide common core services, such as memory management, task scheduling and user interfacing, among others.

Basic firmware

Software embedded into hardware to control the hardware. For instance, the algorithms to decode the video and audio information broadcasted by the transmitter can be implemented in hardware.

The software is stored in a general-purpose memory 102. Typically, the memory 102 would include a Read Only Memory (ROM) portion that contains data intended to be permanently retained such as the program code that the processor 100 executes. In addition, the memory 102 also includes a Random Access Memory (RAM) portion that temporarily holds data to be processed. The memory 102 can be implemented as a single unit, for instance as a semiconductor-based module or may include a combination of a semiconductor-based module and a mass-storage device, such as a hard-drive.

A Universal Serial Bus 104 (USB) port is provided to allow the electronic device 16 to connect to external devices. Specifically, the USB port 104 allows linking the electronic device 16 to a computer that can either download information from the electronic device 16 or upload data to it. For instance, the download process may be used when desired to transfer data stored in the memory 102 to the external computer. Similarly, the upload process is used to perform the reverse operation. This is useful when desired, for example, to change the program running the electronic device 16, by installing one or more updates. The USB port 104 requires a suitable driver that is loaded and executed by the processor 100 when the electronic device 16 is powered up.

A removable storage media reader/writer 106 is provided to allow the electronic device 16 to read data or write data on a removable storage media such as a memory card. This feature can be used to permanently record event-related content that is sent to the electronic device 16. This functionality will be discussed later in greater detail.

As indicated earlier, the keypad 800 allows the spectator to control the operation of the electronic device 16. The number and type of keys forming the keypad 800 is a matter of choice depending upon the specific application. As a possible variant, a touch sensitive screen or a voice recognition capability can be used to replace the keypad 800 or in combination with the keypad 800 as a means for command and data entry by the spectator.

The electronic device 16 has a wireless RF receiver and demodulator 110 that senses the wireless RF transmission, demodulates it and delivers it as properly organized and formatted data blocks to a data bus 112. The data thus sent over the data bus 112 is made available to the memory 102, the processor 100, the USB port 104 and the removable storage media reader/writer 106. In a specific example of implementation, the wireless RF receiver and demodulator 110 operates in the Ultra High Frequency (UHF) range, specifically in the sub range of 470 MHz to 806 MHz. A 6 MHz contiguous bandwidth (equivalent to one regular TV channel) is sufficient to transmit the exemplary payload indicated earlier. Alternatively, the transmission may also be made in the 2.5 GHz range.

A video decoder 114 is provided to perform the decoding of the video channels received from the wireless RF receiver and demodulator 110. For clarity it should be mentioned that while the specification refers to the decoder 114 as "video" decoder it also performs audio decoding on the audio information associated with the video streams. The video decoder 114 has a memory 27 in the form of a buffer that will hold undecoded video/audio information representing a certain duration of video channel play. For instance the size of the buffer may be selected such that it holds 5 minutes of video channel play, for each channel. In use, the video/audio information not yet decoded that is received from the wireless RF receiver and demodulator 110 is sent over the data bus 112 to the video decoder 114. The video decoder 114 decodes the video/audio information and then directs it to a display screen 802 to be viewed by the spectator. At the same time the undecoded video/audio information is directed to the memory buffer 27 that starts to fill. When the memory buffer 27 is completely filled, it starts overflowing such that only the last 5 minutes of the video channel play are retained. The same operation is performed on every video channel, with the exception that only the video channel the spectator wants to watch is being decoded and directed to the display screen 802. Accordingly, the memory buffer 27 is segmented in the functional sense into areas, where each area is associated with a video channel.

The audio stream that is associated with the video stream being watched is decoded, converted into an analog format, amplified and directed to speaker/headphones 124 such that the spectator can watch the video stream on the display screen 802 and hear the audio simultaneously.

The ability to retain the last five minutes of video channel play provides the spectator with interesting possibilities. For instance, the spectator can manipulate the data in the memory buffer 27 so as to "playback" a certain video channel content, create fast forward motion, "rewind" motion and record the video/audio information in the memory buffer 27, either in part or the entire content by copying it on a storage media in the removable storage media reader/writer 106. In this fashion, the video/audio information of interest to the spectator can be permanently retained. Moreover, the spectator can see any action that may have been missed by switching channels and then "rewinding" the content of the memory buffer 27 associated with the newly selected channel.

In addition, the spectator can create "bookmarks" to identify a portion of a video feed that they may wish to revisit. A "bookmark" marks a location in the video stream. For instance a "bookmark" can be in the form of a pointer to a specific address of a video feed stored in either the buffer, or stored in the storage media reader/writer 106. When accessing a bookmark it thus suffices to play the video content starting from the address to which the bookmark points to.

Such "bookmarks" may be created by a spectator by selecting an option provided in one of the GUI menus of the user interface. The spectator navigates the menu by operating keys on the keyboard. Those keys may be arrow keys or any other suitable keys. When a selection has been made, the choice or option can be activated by pressing any suitable key such as an "enter" key.

A bookmark can be created when the spectator watches a live video channel and sees action that is of interest. By entering the necessary command a bookmark is created. During playback, the spectator can quickly identify the video images of interest by using the bookmark. The bookmark can also be useful when the spectator wants to copy some of the video content on the removable storage medium in the reader/writer 106. If a bookmark points to video content that is being copied, the bookmark is also copied such that the identification of the events of interest is retained in the copy.

The ability of the spectator to create bookmarks can be used in replacement or in conjunction of the bookmark generation done at the head end 12 and conveyed in the wireless RF transmission. Those bookmarks function in a similar fashion as the bookmarks created by the spectator. When data that represents a bookmark is observed in the information conveyed in the wireless RF transmission, a bookmark is created and stored with the remaining bookmarks.

Once created, the "bookmark" or pointer is stored in the memory 102 of the electronic device 16 such that it can be accessed by the processor 100. Each time a spectator wishes to re-view the "bookmarked" portion of video feed, the handheld electronic device software will cause the video decoder 114 to retrieve the video feed pointed to by the "bookmark" and start playing the video feed from that point. As mentioned above, the video feed is stored in either in the video memory 27 or in the storage media reader/writer 106. In the case where the video feed is stored only in the video memory 27 which works as a circular buffer to replace old video feed with more recent video feed, once the "bookmarked" portion of video feed has been replaced by more recent video feed, the video decoder 114 is no longer able to access that "bookmarked" video feed. As such, in the case where the spectator wants to retain the "bookmarked" video feed for longer than the memory buffer 27 will allow (i.e. 5 minutes for example), the spectator must transfer that portion of video feed into the storage media reader/writer 106.

The ability to create "bookmarks" provides the spectator with the ability to quickly refer back to a portion of video information that they may wish to review. As mentioned above, not only can "bookmarks" be created by a spectator, but they can also be provided to the electronic device 16 directly from the transmitter 14. These "bookmarks" would be presented to the spectator, such that if the spectator wishes to view the portion of video information associated with a specific bookmark, they can easily do so. The "bookmarks" provided to the handheld electronic devices 16 from the transmitter 14, will typically be related to exciting events that occur during the course of the live sporting event, such as a car crash, a car crossing the finish line or any other event that a viewer might have missed and want to re-view.

It is generally found suitable to use a memory buffer 27 in the form of a semiconductor based unit. In applications where large memory capacity is required in order to store a large video content, a storage device such as a hard drive can be used.

The display screen 802 can be of any suitable type. One possibility is to use a 3.5 in diagonal transrelfective Thin Film Transistor (TFT) screen capable of rendering 320×240 pixel resolution images with 16 bit color depth. Evidently, other display types can be used without departing from the spirit of the invention. Optionally, the electronic device 16 can be provided with a lighting system (not shown in the drawings) using Light Emitting Diodes (LEDs) to facilitate viewing under low light level conditions.

The audio decoder 120 functions in a somewhat similar manner to the video decoder 114. Specifically, the audio decoder 120 is associated with an audio memory buffer 29 and it handles the audio streams conveying the audio information from the independent audio feeds 32 (independent audio streams). The independent audio streams are stored in a compressed format in the audio memory buffer 29 so as to record a predetermined period of the audio content that is received.

By storing the audio content received by the electronic device 16 over a time period determined by the capacity of the audio memory buffer 29, the spectator is provided with the ability to "playback" the audio content, create "fast-forward", "rewind" and bookmarks. In addition, the audio information in the audio memory buffer 29 can be recorded either in part or in its entirety by copying the content on a storage media in the removable storage media reader/writer 106. Bookmarks, as described above, can also be created for audio information.

The functionality of the electronic device 16 will now be discussed in detail.

1. Handheld Electronic Device Authentication

Figure 5:
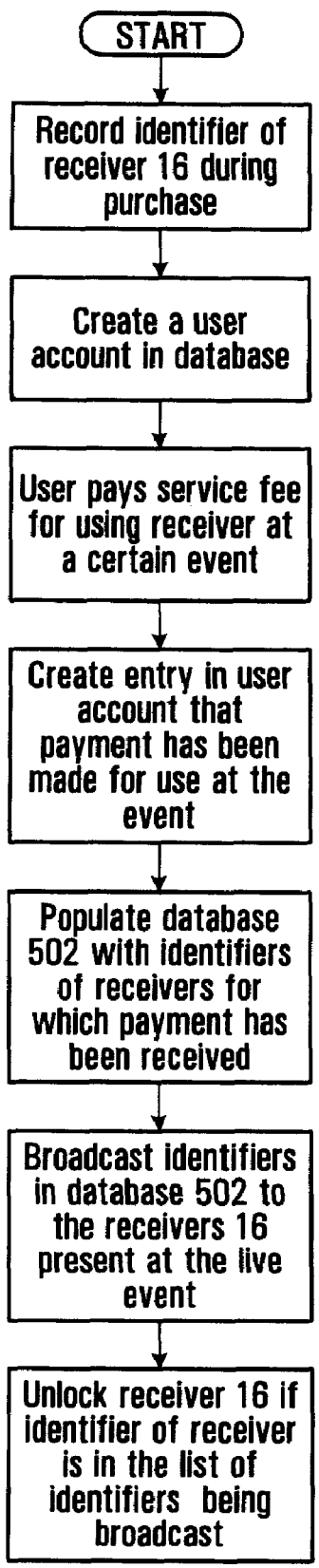
FIG. 5 is a flow chart illustrating a handheld electronic device authentication process.

The flowchart in FIG. 5 illustrates the general electronic device 16 registration process that also covers the authentication feature. When the spectator purchases the electronic device 16 the vendor will record the unique identifier of the electronic device 16. The identifier can be any code, such as a string of numbers or characters that is assigned to the electronic device 16 such that it can be distinguished from other handheld electronic devices 16. Typically, the identifier is a binary code that is permanently stored in the handheld electronic device 16 and thus unalterable. The processor 100 can readily access this binary code when the handheld electronic device 16 is in use. For convenience this unique identifier can be placed on a removable sticker on the electronic device 16 or on the box in which it is shipped from the manufacturer. The identifier can be printed as a bar code that can be read by a machine, such as a bar code reader, can appear as alphanumerical characters or both. In this fashion the clerk performing the transaction can record easily the identifier without having to extract it from the electronic device 16.

At the next step, once the identifier has been recorded, the vendor will typically create a user account in a database. Another option is to allow the user to create online his/her account. This option is discussed later. The user account will allow the user to purchase the delivery of content to the electronic device 16. In the example described in FIG. 5, the user purchases content access on an event basis. In other words, for each event the user wishes to attend, the user will make a payment and the delivery of service will only be available for that event. Evidently, other options exist. For example, the user may purchase access to content on a subscription basis, such as to have access to content over a predetermined period of time for all events within that period. In addition, the account may be designed to allow for different levels of service, such as basic or high grade. A higher grade service, for example, offers features to the user not available under the basic level.

Continuing with the above example, assume that the user now whishes to have access to content on the electronic device 16 for a certain live sporting event that the user plans to attend. The user then makes the payment to his account. The payment can be made in person, to a kiosk or at any other location authorized to receive payments. Advantageously, electronic payment methods, such as over the Internet, can be used. With such a method the user logs on to an Internet site of the service provider and makes the payment via credit card or other. The payment process will typically include selecting the event or group of events for which access to content is desired, the level of service, if applicable, and then making the payment. When the payment is made and validated an entry is automatically made in the user account indicating that access to content for the electronic device 16 specified in the account is enabled. A detailed example of an on-line service delivery purchase is provided later in the specification.

At the event itself, before starting to broadcast the content to the individual handheld electronic devices 16, the database 502 connects to the network of the service provider over the Internet such that the database 502 can be populated with the identifiers of all the handheld electronic devices 16 for which payment for content delivery for the event has been made. Once this step is completed all the electronic device 16 identifiers in the database 502 are transmitted to the head end 12 such and they are all included in the broadcast that is made by the transmitter 14. Specifically, the block of identifiers are broadcasted periodically, say every minute such as to allow the individual handheld electronic devices 16 to perform the authentication process at any time.

Each electronic device 16 is designed such that it cannot operate unless it has been electronically unlocked. When the electronic device 16 is powered up, it automatically enters the locked mode. During the locked mode the electronic device 16 will acquire the wireless RF transmission and decode the information such as to extract the block of identifiers that are being sent. In this example, the block of identifiers constitute the authentication data that determines if a particular electronic device 16 will be allowed to receive the service or not. Once the block of identifiers are extracted from the transmission the electronic device 16 will compare each code from the block to the identifier of the electronic device 16. If a match is found, then the electronic device 16 enters the unlocked mode and the content that is being broadcast can be adequately received. However, if no match is found after a certain period, say 2 minutes the electronic device 16 shuts down automatically.

The approach described earlier is a simple way to ensure that content is delivered only to spectators that have made payment, since no encryption of the video/audio content is required. In addition, the delivery of the authentication information to the individual handheld electronic devices 16, such as the block of identifiers, in a wireless manner, is simple from a logistics standpoint.

For enhanced security, the block of identifiers that are being transmitted can be encrypted using any suitable encryption techniques. The electronic device 16 should, therefore be provided with capability to decrypt the block of identifiers by using a suitable key.

Another option is to encrypt the entire transmission and require the electronic device 16 to decrypt it. In this form of implementation, the encryption constitutes the authentication data carried by the wireless RF transmission that is processed by the individual handheld electronic devices 16. A decryption key or password may need to be input by the spectator to allow a electronic device 16 to be unlocked. In such case, a decryption key may be provided to the spectator following the payment for the service. When the spectator powers up the handheld electronic device 16, the spectator enters the key and that key is used to perform the decryption.

If encryption or decryption is required, the function can be implemented at the electronic device 16 by suitable software or hardware, both of which are known in the art.

The authentication described earlier can be modified such as to provide service level access control. As it will be discussed later, the handheld electronic device 16 can be designed in such a way as to deliver to the spectator service available in different levels or categories. The levels can be distinguished from each other on the basis of content, for example. The basic level of service may include basic content, such as for example a limited number of video channels. A higher level of service may include a larger number of video channels and contextual information or other content. The reader will appreciate that the distinguishing characteristic of the different service levels will vary in accordance with the intended application. Generally, the higher the service level, the richer the content it provides to the spectator.

The service levels are likely to be available at different cost to the spectator. More specifically, the basic level of service is likely to be the least expensive and as content options are added to upgrade to a higher level of service then the cost to the spectator will increase.

It is desirable to provide the handheld electronic device 16 with an authentication feature that will allow the handheld electronic device 16 to provide to the spectator access to the level of service the spectator has paid for and thus protect the wireless RF transmission from unauthorized access to content or service levels that have not been purchased.

One possible option is to create when the spectator purchases the service distinct lists of identifiers for each service level that is available. Assume that three service levels are available, namely service level A, service level B and service level C. Service level A is the basic and the least expensive. Service level B is the intermediate level and includes features not available under service level A, for example more video channels and a limited amount of contextual information. Service level C is the highest and it provides the richest content, namely the largest number of channels and the most contextual information. As the service is being purchased by spectators, three different lists of electronic identifiers are created, one for those that have purchased service level A, one for those that have purchased service level B and for those that have purchased the service level C.

Under this example, the wireless RF transmission is structured in a way to maintain a distinction between the different levels of service. For example, a core block of frames carries the content for the service level A, which is the basic level. A first additional block of frames carries the additional content that is added to the service level A to upgrade to service level B. Finally there is a second additional block of frames that carries the additional content added to service level B to upgrade to service level C. In such case, the service level C encompasses the content of service levels B and A, while the service level B encompasses the content under service level A.

The authentication information sent to the handheld electronic devices 16 is organized into groups as well. There is a first group that contains the list of the identifiers of the handheld electronic devices 16 for which service at level A has been purchased, a group with a list of the identifiers of the handheld electronic device 16 for which service at level B has been purchased and a list of the identifiers of the handheld electronic devices 16 for which service at level C has been purchased.

As a handheld electronic device 16 picks up the wireless RF transmission, it will, as discussed earlier try to find in anyone of the lists its own electronic identifier. If the identifier is not found in anyone of the lists, then the handheld electronic device 16 will not unlock itself and the spectator will not be able to access the content. However, the handheld electronic device 16 will unlock itself if its identifier is found in anyone of the lists. If the identifier is found in the list for service A, then the spectator will be able to view only the content carried in the core block of frames, the one that is associated with the service level A. Access to frames associated with any other service level will not be allowed. The control is implemented by the handheld electronic device 16 that determines which part of the wireless transmission it can make available to the spectator. Since the different block of frames are clearly distinguished from one another and associated with the respective groups of identifiers, the determination of the groups where the identifier of the handheld electronic device 16 resides, allows controlling the access to the relevant block of frames that hold the content. If the identifier is in the group associated with the core block of frames, only those will be processed and in effect the spectator will have only access to the service at level A. If the identifier of the handheld electronic device 16 is located in the group associated with the first additional block of frames then only the core block and the additional bloc will be processed, in effect limiting access to the content at level B. Finally, if the identifier of the handheld electronic device 16 resides in the group associated with the second additional block of frames, then full access to the entire content is granted.

The examples of the authentication feature described above are relatively simple to implement. However, there is a need to carry in the wireless RF transmission the entire list of the electronic identifiers of the handheld electronic devices 16 that are allowed to receive content. If a large number of handheld electronic devices are being serviced by the wireless RF transmission, the number of electronic identifiers that need to be transmitted may grow too large to be practical.

Figure 25:
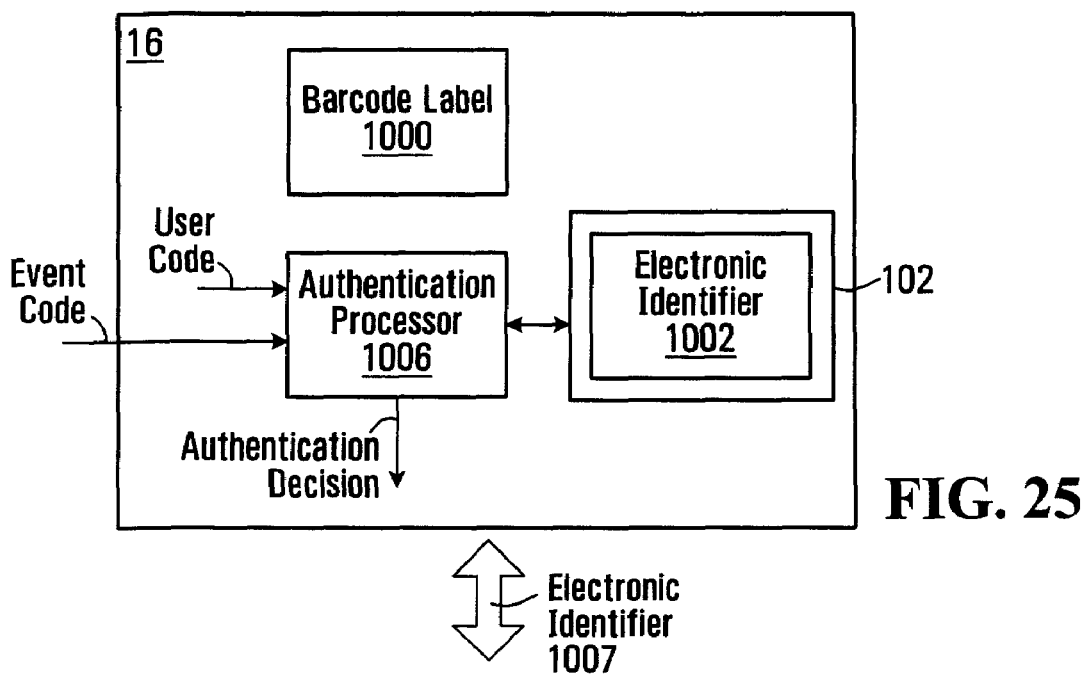
FIG. 25 is a high level block diagram of the handheld electronic device showing components to perform authentication function.
Figure 26:
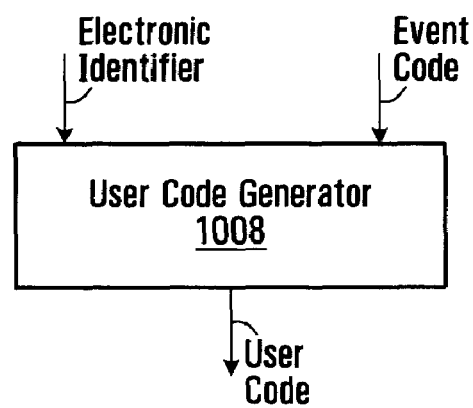
FIG. 26 is a block diagram of a processor that is external of the handheld electronic device to generate a user code.
Figure 27:
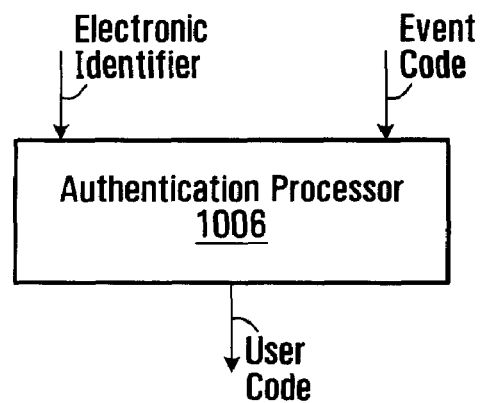
FIG. 27 is a block diagram of an authentication processor shown in FIG. 25.

FIGS. 25 to 27 illustrate a variant in which it is not necessary to include in the authentication information in the wireless RF transmission a complete list of the handheld electronic receivers 16 allowed accessing the content in the wireless RF transmission. FIG. 25 shows a high level block diagram of the handheld electronic device 16 illustrating the storage area (which includes the memory 102 in addition to any other storage, either volatile or not volatile). The non-volatile portion of this storage area holds the electronic identifier described earlier. In this drawing the electronic identifier is designated by the reference numeral 1002.

The handheld electronic device 16 is also provided with a bar code 1000 on its casing that is machine readable, such as by using a bar code reader (not shown). The bar code is a representation of the electronic identifier 1002. Note that the label holding the bar code may also contain another form of representation of the electronic identifier 1002, such as for example by using alphanumeric characters suitable to be read by a human.

It is also possible to apply on the casing of the handheld electronic device 16 a bar code 1000 that is not identical to the electronic identifier 1002. In other words, the electronic identifier 1002 and the bar code 1000 are different codes. Some embodiments of the authentication process described later require access to the electronic identifier 1002 via the bar code 1000. In the embodiment where the electronic identifier 1002 and the bar code 1000 are the same codes then a reading of the bar code 1000 will yield the electronic identifier. However, when they are different codes, a mapping mechanism can be used to relate one to the other. The mapping mechanism can be a database storing all the population of electronic identifiers 1002 and the respective bar codes 1000. When it is necessary to obtain an electronic identifier 1002 of a certain handheld electronic device 16, the bar code 1000 is read, the database searched and the corresponding electronic identifier 1002 retrieved.

The handheld electronic device 16 also includes an authentication processor 1006. The authentication processor 1006 is designed to handle authentication related tasks, such as for example output the electronic identifier 1002 to an external device (as it will be described later), process a user code entered by the spectator and the authentication information contained in the wireless RF transmission to electronically unlock the handheld electronic device 16 to allow the spectator to gain access to the content in the wireless RF transmission. The authentication processor 1006 is likely implemented in software but it can also be implemented in hardware by a specialized circuit. A combination of software and hardware is another option.

When a spectator desires to purchase the delivery of service to the handheld electronic device 16, the spectator performs the transaction by interacting with an external entity which generates a user code. At the live event, the spectator enters via the user interface the user code provided earlier. The authentication processor 1006 performs a validation of the user code information provided by the spectator and issues an authentication decision. The authentication decision is conveyed by any suitable internal signal which will have the effect to allow the spectator to gain access to the content in the wireless RF signal, If the user code is a correct code, or to deny this access when the user code is a wrong code. For instance, the signal that conveys the authentication decision can be designed to enable the processing of the content in the wireless RF transmission such that it can be viewed and/or heard by the spectator, when the authentication decision validates the user code. On the other hand, when the authentication decision does not validate the user code, then the internal signal is designed to prevent content from being made available to the spectator. The authentication decision issued by the authentication processor 1006 can also be designed to handle levels of service. In such case, the authentication decision indicates which level of service the handheld electronic device 16 is entitled to receive, if any.

A block diagram of the external entity is shown in FIG. 26. More specifically, the external entity has a user code generator 1008 which receives as inputs the electronic identifier 1002 and the event code. The user code generator 1008 processes these entries by any suitable function which produces the user code. The function uses as parameters the electronic identifier and the event code and processes them mathematically. The user code is the result of the mathematical processing. The mathematical processing itself is not critical to the invention and many different mathematical functions can be used without departing from the spirit of the invention. One desirable property of the mathematical processing is that it should be non-reversible. By non-reversible is meant that knowledge of the user code does not allow reconstructing the electronic identifier 1002, nor the event code, nor the mathematical function used to generate the user code based on the two inputs.

The user code generator 1008 can, for example, be implemented at a booth at the live sporting event the spectator plans attending. The attendant at the booth receives payment from the spectator, the amount of which may be dependent on the level of service desired. The attendant then places adjacent the handheld electronic device 16 a reader such as an infrared reader to interact with an infrared port (not shown in FIGS. 25 to 27) on the handheld electronic device 16. The infrared reader and the handheld electronic device 16 establish communication and the authentication processor 1006 releases over the infrared link the electronic identifier 1002. The infrared link is depicted in FIG. 25 by the large arrow 1007. Alternatively, communication between the handheld electronic device 16 and the reader can be established by using a wireline connection such as via a USB port, or any other suitable arrangement.

The electronic identifier is supplied to the user code generator 1008 in addition to the event code which is available to the user code generator 1008. Normally, the same event code is used for every handheld electronic device 16 for which service is being purchased. The event code is a code that designates the event for which service is being purchased, while the electronic identifier is a code that distinguishes one handheld electronic device 16 from another. In a specific example of implementation the event code will typically be different from one event to another. For instance, in the case of motorsports applications, different event codes will be attributed to different races during the season in a given year.

The user code generator 1008 will process the two entries according to the desired mathematical non-reversible function and outputs the user code. In this particular case, the mathematical processing is a succession of mathematical operations on the two entries that produce a user code that is smaller (less digits) than both the event code and the electronic identifier 1002. The user code is given to the spectator in any convenient way. It may be printed, for instance on a ticket and remitted to the spectator. Normally, this code will be unique to each handheld electronic device 16.

Note that it is also possible to implement the user code generator 1008 to produce user codes for different handheld electronic devices 16 without establishing an electronic communication with the handheld electronic devices 16. This can be done by using a bar code reader for reading the bar code 1000 on the casing of each handheld electronic device 16. If the bar code 1000 is the same as the electronic identifier 1002 then the processing by the user code generator 1008 can be effected as described earlier. Otherwise, if the bar code 1000 is different from the electronic identifier 1002, a database (not shown) mapping the bar codes 1000 to the electronic identifiers 1002 of the population of the handheld electronic devices 16 is searched to extract the electronic identifier 1002 corresponding to the bar code 1000 that was read.

As the spectator enters the stadium, the spectator turns the handheld electronic device 16 on and he is requested by the authentication processor 1006 to supply a user code. The request may be, for example, a prompt appearing on the display 802 of the handheld electronic device 16 to enter a user code (assuming that the system requires manual input of the user code). The spectator enters the user code printed on the ticket via the user interface of the handheld electronic device 16. The authentication processor 1006 to which are readily available the electronic identifier 1002 and the event code that is conveyed in the wireless RF transmission, processes the electronic identifier 1002, and the event code according to the same mathematical function implemented by the user code generator.1008. If the output of the process issues a code that matches with the user code entered by the spectator, then the authentication processor 1008 issues an authentication decision allowing access to the content in the wireless RF transmission. Otherwise, access to the content is denied.

A possible option is to communicate the user code to the handheld electronic device 16 electronically, immediately after the electronic identifier 1002 is communicated to the user code generator 1008. As soon as the user code generator 1008 computes a user code, that code is conveyed via the communication link 1007 to the authentication processor 1006. This option obviates the need for the spectator to manually input the user code for validation purposes. The electronic transaction 1007 automatically unlocks the handheld electronic device for use at the live sporting event, without the necessity for the spectator to input any user code.

In a possible variant, the user code is provided to the spectator via an online purchase set-up that can be made any time before the live event begins. The principles of this arrangement are described later. Briefly, the spectator accesses the Internet via a personal computer or any other communication device and connects with a web site where an on-line purchase of delivery of service can be made. The server hosting the web site implements the user code generator and computes a user code. The user code that is produced is communicated to the user, such as by displaying it on the screen of the personal computer, sent to the user by e-mail to a specified e-mail address or via any other suitable fashion. The user will retain the user code and enter it in the handheld electronic device 16 during the live event.

Another possible option that can be considered is to convey in the wireless RF transmission, the event code (as in the previous embodiment) and also all the user codes for the handheld electronic devices 16 for which service has been purchased. This option would require computing for every handheld electronic device 16 for which service is purchased (for example at the point of purchase of the service) a user code and storing all the user codes so computed into a database. During the live sporting event, the content of the database is periodically broadcasted along with the event code. Each handheld electronic device 16 that is at the live sporting event receives the wireless RF transmission and extracts the event code. The event code is then used to compute a user code by the authentication processor 1006. That user code is then checked against the set of user codes contained in the wireless RF transmission. If a match is found the authentication processor 1006 issues an authentication decision allowing the handheld electronic device 16 to access the video/audio content in the wireless RF transmission. If no match is found then the handheld electronic device 16 remains locked.

The various embodiments described above that employ a user code for authentication purposes can also be adapted to a multi-service level arrangement. In the case of a multi service level system, the spectator will be provided with a different user code depending on the particular service level that was purchased. The wireless RF transmission has content that is structured to distinguish one service level from another and each service level is associated with different authentication information. The authentication information is a compound event code including a plurality of service level codes that are different from one service level to another. Accordingly, in this example, the authentication information will contain as many service level codes as there are different service levels. In use, the authentication processor 1008 will try to match the user code supplied by the spectator to the compound event code. Specifically, the authentication processor 1008 will issue an authentication decision to unlock the handheld electronic device 16 when a match is established between the user code and any one of the service level codes, but the authentication decision will control the access to the content, as discussed earlier, such that the spectator will only be able to gain access to the service level that was purchased.

Note that the event codes (either a unique code or a compound code in the case of a multi-level approach) are generated by the authority or organization controlling the delivery of service to the spectators during the live event. Those codes can be randomly generated for every new event.

2. Video Stream Reception and Related Functions.

Assuming that the authentication process described earlier has been successfully passed, the graphical and navigational layer is loaded and the user interface that allows the spectator to access the various functions is presented on the display screen 802. Typically, the user interface presents a menu that will show a list of choices. The spectator navigates the menu by operating keys on the keyboard. Those keys may be arrow keys or any other suitable keys. When a selection has been made the choice or option is activated by pressing any suitable key such as an "enter" key.

The menu options available to the spectator can vary significantly according to the intended application. The description provided below illustrates a few possible examples.

Watching a video channel—the spectator will access this choice and activate it. The menu hierarchy is designed so as to display the list of the possible video channels that the spectator can watch onscreen. The spectator selects the one he or she desires by pressing the appropriate selection keys and confirming the choice by pressing the "renter" key. At this point, the handheld electronic device software will instruct the video decoder 114 to start decoding the appropriate channel. The decoded video information will be directed to the screen and it will be displayed to the spectator. At the same time the audio output is played by the speaker/headphones 124.

At any time the spectator can invoke the graphical interface to either stop the video watching or switch to a different video channel.

One option that may also be considered is to view thumbnails of video channels onscreen so as to allow the spectator to select the one he or she finds the most interesting. Specifically, the spectator invokes the thumbnail option on the graphical user interface and as a result he/she sees on the screen a plurality of thumbnails, each associated with a given video channel. The number of thumbnails can vary according to the intended application. In one possible example four thumbnails are presented, each associated to a video channel, with each thumbnail thereby occupying a quadrant of the screen. A total of 10 video channels will require two and a half-thumbnail pages for the spectator to see. The spectator can switch from one thumbnail page to the other by pressing appropriate keys on the keypad 108. When the spectator desires to watch the video channel from a particular thumbnail, he/she selects that thumbnail to expand the image and cause it to occupy the entire screen.

The thumbnail function requires the video decoder 114 to process several video channels at the same time. The processing is done such that the resolution is decreased sufficiently to reduce each image to a portion that will fit in the thumbnail space. When four thumbnails are displayed on the screen, the resolution of each video feed 31 is reduced by a factor of four.

When viewing thumbnail pages, different options exist in handling the audio stream associated with the corresponding video feeds. First, the audio stream may be interrupted altogether since each page is associated with multiple audio streams. The audio stream may be activated only when the spectator has selected to view a video channel over the entire screen. In a possible variant, the spectator is provided with the option of highlighting thumbnails as he/she navigates through them by pressing selection keys on the keypad 108. As a thumbnail is highlighted, the audio stream associated with that particular video stream is decoded and directed to the audio output. Once a thumbnail is highlighted, it can be selected and thus expanded to full screen by pressing any appropriate key, such as the "enter" key.

In addition to the purely manual method for selecting the video channel to watch, the system can be designed to perform some automatic video channel switching based on some particular parameters. This will be described later in greater detail.

Data overlay—the spectator can choose to see data content that is overlaid on the screen of the electronic device 16. In a first example, In one non-limiting example, the real-time data content includes information relating to the live sporting event, such as for example scoring and participant ranking information, among others. In the specific example of a car racing event, the real-time information can include the current ranking, number of laps remaining, participants still in the race, participants no longer in the race, fastest lap of the current leader or of anyone of the participants, average speed of the current leader or of anyone of the participants, among others. In another example, the real-time data content can also convey physiological information associated with anyone of the participants. Again in the context of a car race, the physiological information can include the heart rate of the driver or his body temperature, among others. The real time data content is usually available from the authority sanctioning the live sporting event. In the case of the physiological information, a requirement would be to provide one or more of the participants with the necessary sensors that measure the heart rate, body temperature, etc and convey the collected information to the head end 12 such that it can be included in the wireless RF transmission. It is not deed necessary to describe in detail how the physiological information is collected and delivered to the head end 12, since this would be known to a person skilled in the art.

When the data is not video channel specific, it can be organized as a "ticker" type band that appears at any appropriate location on the screen and continually cycles time and scoring information that is updated in real-time. With this example, the same information is seen on each video channel.

In a second example, each video channel is provided with associated data content. A video channel specific data content may include the name and other identification information associated with the race team or car being watched, current standing, best lap time, among others.

When the amount of information to be displayed is relatively small, it may appear as a static overlay in contrast to a "ticker" approach. The data in the static overlay is changed only when necessary to update it.

In order to provide as much flexibility as possible, options may be presented on the screen so as to allow the spectator to see additional information of interest. Specifically, the screen shows areas suggesting tabs that can be selected by pressing selection keys on the keypad 108. Each tab provides access to a lower level of additional information that will then appear in the data overlay. Such additional information may include information on the driver's career, information on the driver's vehicle, promotional information about the driver's team or paraphernalia, among many others.

With video channel specific data content, it is useful to structure the data content that is being broadcast in a way that creates a logical association with the respective video feed 31. For instance, the data that is carried into the data packets being broadcast can be grouped into blocks, each being associated with a given video channel. Additional blocks may be provided that correspond to the data that may be shared by all the video channels or a subset of the video channels.

When such an association is created the video channel specific data content can automatically be shown in the overlay as soon as the video channel is selected for viewing.

Figure 6:
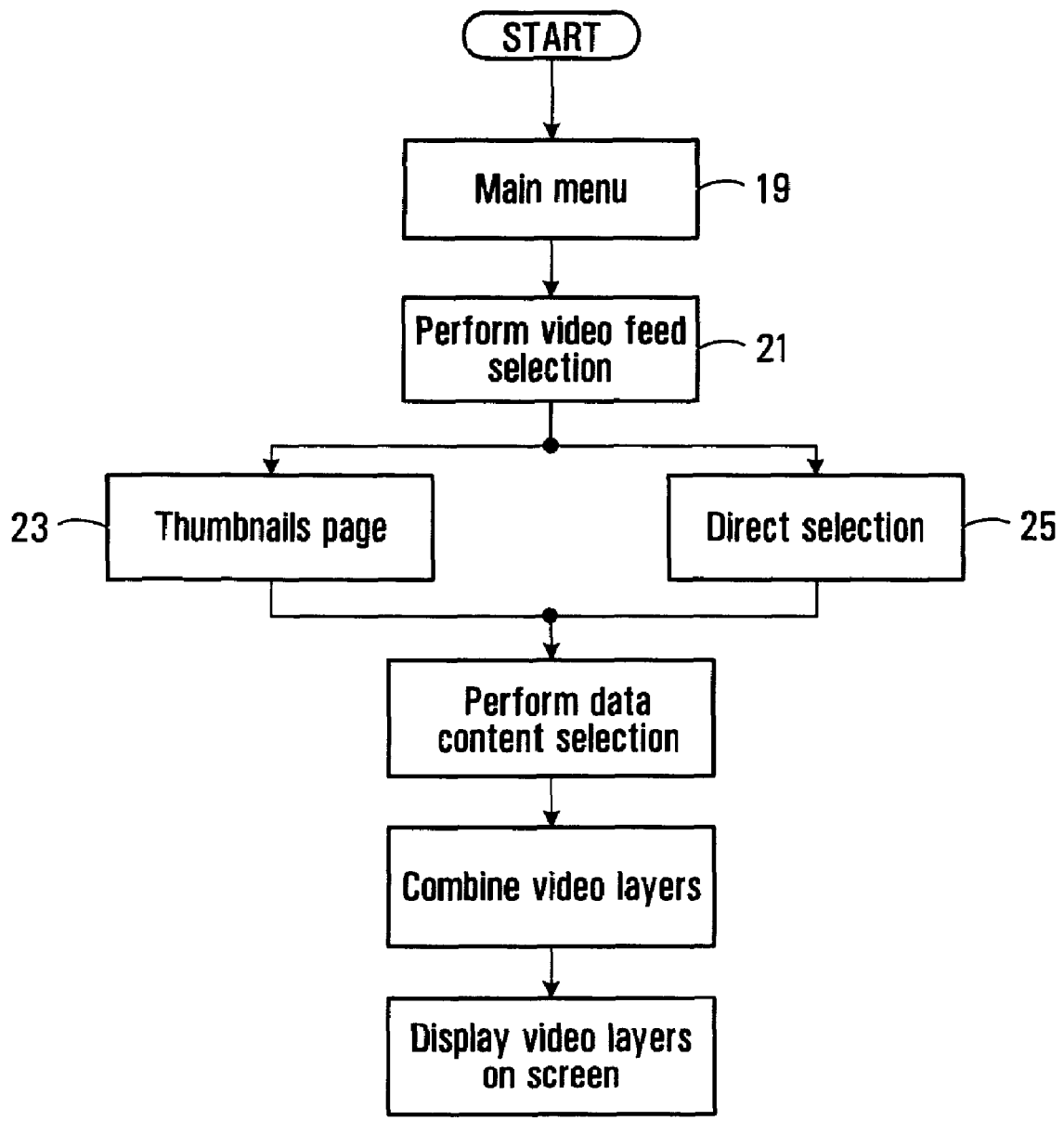
FIG. 6 is a flow chart illustrating a video viewing process.
Figure 7:
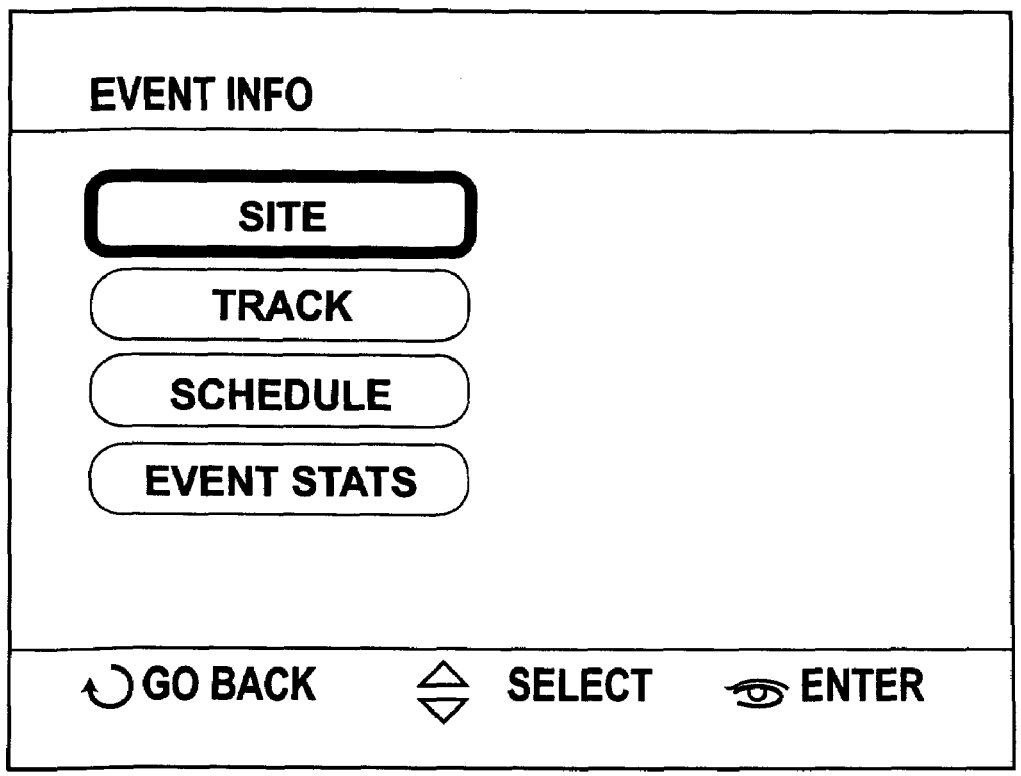

The flowchart in FIG. 6 summarizes the video viewing process. The spectator accesses the main menu 19 from which he/she navigates to the video channel selection commands 21. Those commands can be grouped into thumbnail page commands 23, or direct selection commands 25. The thumbnail page commands allow the spectator to view real-time video channels in thumbnail size and to select one for full screen viewing. The direct selection command allows the spectator to directly specify the video channel for full screen viewing. At the next step the data to be overlaid is selected. The data and the video information are overlaid and shown on the screen.

Video playback functionality—Since the video channel content is being continuously buffered, the spectator has the ability to implement a video playback functionality by selecting which portion of the video content currently in the memory buffer 27 will be displayed on the screen. The degree of playback depth, in other words the extent to which the spectator can wind back the video content, depends on the memory buffer 27 size. As suggested earlier this size may be selected to accommodate a 5 minute playback depth. Of course, this is one possible example that should not be construed in a limiting manner.

The spectator can invoke the playback feature on the user interface. For example, the spectator accesses a menu item with the appropriate selection keys and then confirms by pressing the "enter" key. When the playback feature is active, the following functions are available:

Rewind—the rewind function positions the pointer in the memory buffer 27 at a previous location. The speed at which the spectator effects the rewind can be set or can be selectable. During the rewind, two options exist. One is to show a blank screen and resume video play when the rewind key has been released. The video play will start at the location to which the pointer in the memory buffer 27 has been pushed back. The other option is to see the video content played in reverse while the "rewind" is active so as to allow the spectator to more easily find an image or section of the video content of interest. The speed at which the video content is played back as the memory buffer 27 is being backed up, can be fixed or variable, under control of the spectator.

Fast forward—opposite of the rewind function. Can be invoked only when the pointer in the memory buffer 27 has been backed up to some degree.

Bookmark—the spectator can jump to a certain point in the video content by selecting a previously established "bookmark" from a menu option, as described earlier. Each "bookmark" points to a specific portion of the video feed in the memory buffer. As such, when the spectator selects a "bookmark", the video play will start at the location of the pointer associated with the bookmark. The "bookmark" function enables the spectator to quickly jump back and forth to interesting portions of video play. The bookmark feature also allows the spectator to jump quickly from one bookmark to another bookmark. In this fashion, the spectator can easily go from one salient event to another in the video content held in the video memory 27 without the necessity of fast forwarding or rewinding the video content.

Still image—the spectator can pause the image which is effected by maintaining the pointer in the memory buffer 27 at a fixed location. In this manner, the spectator sees the same image frame.

Moving frame by frame—the spectator can see the image moving (by "moving" is meant either a forward movement or a backward movement) slowly frame by frame at a pace slower than the normal frame rate. Pressing the appropriate key on the keyboard can allow the image to jump from one frame to the next. Alternatively, the image can be moved automatically frame by frame but at a slower than normal rate so as to allow the spectator to see each frame individually.

Zoom—the spectator can zoom in or out on frames shown on the screen. Typically this function is enabled when the still image feature is active. The zooming in can be invoked by pressing one key on the keypad 108, while the reverse, zooming out function can be invoked by pressing a different key.

Video recording—the spectator can transfer some or the entire video stream content in the memory buffer 27 to the removable storage media in the storage media reader/writer 106. Again, operating the appropriate keys on the keypad 108 enables this function. Several options exist:

Start recording the video content that is being played in real time on the screen. This function is useful when the spectator sees footage that is of interest and that he/she would like to record. The video content that is directed to the video memory buffer 27 is also copied in a compressed form to the removable storage media 106. In this fashion, the video content can be played back on the electronic device 16 or on any other suitable electronic device that can read the video information stored in the removable storage media 106. The amount of video information that can be recorded on the removable storage media 106 depends on the size of the storage media.

Transfer the entire content of the memory buffer 27 to the removable storage media 106. This option is possible if the size of the removable storage media 106 can accommodate the information in the memory buffer 27.

Transfer only a selected portion of the memory buffer 27 to the removable storage medium 106. This function can be activated by first performing a "rewind", "fast forward" or a "frame by frame" movement until the desired location in the memory buffer 27 of interest has been reached, and then activating the "play" and "recording function" that will start transferring the compressed image stream to the removable storage medium. When the desired portion of the video content has been recorded on the removable storage medium 106 the spectator can stop the recording process.

Any bookmarks entered by the spectator are also transferred to the removable storage medium 106. This is effected by copying on the removable storage medium 106 the address of the video information to which the bookmark points to. In this fashion, the if the spectator has placed bookmarks during the watching of the live sporting event those are not lost when the video content is transferred to the removable storage medium 106.

3. Audio Stream Reception and Related Functions.

The following examples focus on the delivery of the independent audio streams since the handling of the audio streams associated with the respective video streams was described in the earlier section.

As indicated earlier, the independent audio streams convey radio conversations between members of a race team (typically an audio stream will be associated with each race team), audio commentaries about the race or advertisement information, among others. At the electronic device 16 the spectator can manually select anyone of the streams and direct them to the output 124 which drives a sound reproducing device such as a loudspeaker or headphones. Another possibility exists which allows the spectator to define a priority profile such as to play the audio streams according to an order of priority.

The order of priority is defined by storing in the electronic device 16 priority profile data. More specifically, the priority profile data is stored in the memory 102 or any other suitable memory that allows the processor 100 to access it readily. For convenience, the priority profile data may be stored in a non-volatile section of the memory 102 such that the information will be retained even after the electronic device 16 is powered down, thus avoiding re-entering the information again every time the electronic device 16 is powered-up.

The priority profile defines an order of priority according to which the audio streams will be played. The following is an example of a priority profile:

| | |
|---|---|
| Priority 1 (highest) | radio conversations of team C |
| Priority 2 | radio conversations of team A |
| Priority 3 | radio conversations of team K |
| Priority 4 | audio commentary about the race |
| Priority 5 | advertisement content |

The software that runs the electronic device 16 includes a module that provides the function of an audio stream selector. The audio stream selector which may be part of the user interface of the handheld electronic device 16 decides which one of the audio streams contained in the wireless RF transmission to play based on the priority profile. Before enforcing the priority profile the audio stream selector will distinguish the active audio streams from the inactive audio streams in the wireless RF transmission. An active audio stream is an audio stream that conveys some type of information the spectator can understand. In contrast, an inactive audio stream is a stream that that conveys no such information. A typical active audio stream is an audio stream conveying a conversation, while an inactive audio stream only conveys silence or low intensity noise. One way to distinguish between an active audio stream and an inactive one is to analyze the data conveying the audio information and ascertain what the signal level is. A high signal level likely denotes an active audio stream while a low signal level likely denotes an inactive audio stream. The reader skilled in the art will appreciate that many signal analysis techniques are available in the art allowing distinguishing between an active audio stream from an inactive one and no further description is required here.

In an alternative embodiment, each audio signal is encoded with an indication as to whether that signal is active or inactive by the audio processor 42 at the head end 12. This characteristic was described earlier and will not be discussed again. As such, the audio signal selector at the electronic device can determine based on the encoding of the signal whether it is active or inactive. This would avoid having to use any analysis techniques at the handheld electronic devices 16 in order to determine an inactive and active audio stream.

Assume for example that the electronic device 16 receives 10 audio streams, where streams 1-8 are associated with respective racing teams, audio stream 9 conveys an audio commentary and audio stream 10 conveys advertisement information. After performing the activity analysis on the audio stream, the audio stream selector classifies the audio streams as follows:

Active
Audio stream 1 (team A)
Audio stream 5 (team K)
Audio stream 7 (team B)
Audio stream 9 (audio commentary)
Audio stream 10 (advertisement content)

Inactive
The remainder of the 10 audio streams.

The audio stream selector will then search the active list for the audio stream in the highest level of priority in the priority profile. This position corresponds to team C that is not in the active list. Next the audio stream selector searches the active list for the entry in the priority profile having the second order of priority. This corresponds to team A which is associated with the audio stream 1. Since this audio stream is active the audio stream selector will play it to the spectator by directing it to the output leading to the loudspeaker or headphones.

The scanning of the audio streams to identify the active ones and the inactive ones is effected periodically, such as every 15 or 30 seconds and if there is any audio stream having a higher order of priority than the one currently played, it is directed to the output. In this fashion, the spectator is always presented with the audio stream information that is the most relevant or of interest to him/her.

Optionally, the spectator interface of the electronic device 16 can be designed to allow the spectator to stop the periodic scanning of the audio streams and continue playing the audio stream that is being currently selected.

In order to somewhat simplify the construction of the electronic device 16, the head end 12 may be designed such as to perform the audio stream activity analysis and insert in the payload information to that effect. As indicated previously, the audio streams are broadcasted in the form of packets, where each packet may contain audio information for a single audio stream or audio information for a collection of audio streams, depending on the specific packet structure selected for the intended application. For a given block of audio data corresponding to a certain playing time for a given audio stream, the head end performs the activity analysis and associates with that block a flag to indicate whether the audio information is considered active or inactive, depending upon the value of the flag. In this fashion, each electronic device 16 is always aware of which audio streams are currently active and the audio stream selector can perform the audio stream switching without the necessity of conducting any audio stream activity analysis.

Since the priority profile defines the preference of the spectator, the user interface of the electronic device 16 is designed to allow the spectator to configure the priority profile and modify the profile once an initial configuration has been made. The reader skilled in the art will appreciate that many possible configuration mechanisms can be designed. A simple approach is to present the spectator with a list in which the spectator enters one after the other (decreasing order of priority) the racing teams or other type of content that can be conveyed by the audio streams. The data is then saved in the memory 102 in the form of a file, for example. The audio streams processing is then performed as discussed earlier. Evidently, a mapping operation needs to be performed at some point to associate a racing team name or identifier (if the data in the preference profile is entered in this manner in contrast to directly specifying the audio streams) to the audio stream corresponding to that racing team. For example, mapping information can be sent over the wireless RF transmission to effect this operation.

Another possible refinement is to send in connection with any one of the audio streams a priority flag which denotes content of potentially high interest to the spectators, such as for example conversations between emergency crews in the case of an accident. In such case, the audio stream selector is designed to play that audio stream and override any priority profile settings. If desired the user interface of the electronic device 16 can be designed to disable this function which forces the electronic device 16 to play the audio stream with the high interest flag.

Yet, another possibility that can also be considered is assigning priorities to positions of participants in the race rather than to specific crews or participants. For instance, priority number 1 can be assigned to the race leader, without regard to the particular participant that occupies the position at the time being. A more detailed example of a priority scheme includes the following:

Priority #1—race leader;
Priority #2—second position;
Priority #3—any car in the pits The audio that is currently played is selected according to this priority scheme. If no activity exist on the audio stream associated with the race leader, then the audio selection moves to the priority #2 position, and so on. To enable this functionality, the head end 12 is marking the individual audio streams with data which associates the audio streams with the ranking of the respective participants of teams. In this fashion the electronic device 16 can adequately recognize the various positions of the participants of teams. One example is to insert in a suitable field of the binary transport of the wireless RF transmission information allowing identifying the race positions. By following the above priority scheme each audio stream is described by data that indicates the current position in the race. Also, additional descriptive data is provided to point to the audio streams associated with cars that are in the pits.

A possible variant is to use the real time data contained in the wireless RF transmission to map the various teams with respective race positions. Assuming that the individual audio streams in the wireless RF transmission are provided with suitable team or participant identifiers, the real time data that communicates the positions of the teams or participants can be used to establish the correlation between audio streams and race positions.

While the audio management function described above is done in connection with the electronic device 16 that provides video reception capability, similar audio management functions can also be implemented in simple audio only electronic devices. In the infrastructure described earlier, which uses a head end 12 to build a signal structure conveying an audio/video/data payload, such electronic device can be designed to disregard any video information and process the audio and data information only. With infrastructures that do not use a head end 12, the electronic device can be designed to implement at least some of the functions described earlier while accessing directly the raw audio sources. In such case, the electronic device includes a series of tuners, each tuner being set at a frequency corresponding to a given audio source, for example the frequency used by a race team for communication. In such case, the wireless RF transmission that the electronic device acquires encompasses the group of frequencies to which the tuners are set. Those frequencies may need to be entered manually by the spectator using the electronic device, for example, before the racing event begins. At this point, the audio stream selector analyses the outputs of the different tuners to determine if they are active or not and applies the priority policy defined by the priority profile in determining which audio stream should be played.

Since the audio streams are continuously buffered, the spectator has the ability to implement an audio playback functionality. The degree of playback depth, in other words the extent to which the spectator can wind back the audio content, depends on the memory buffer 29 size. This size may be selected to accommodate a 5 minute playback depth. Of course, this is one possible example that should not be construed in a limiting manner.

The spectator can invoke the playback feature on the user interface. For example, the spectator accesses a menu item with the appropriate selection keys and then confirms by pressing the "enter" key. When the playback feature is active, the following functions are available:

Rewind—the rewind function positions the pointer in the audio memory buffer 29 at a previous location. The speed at which the spectator effects the rewind can be set or can be selectable. The audio play starts at the location at which the pointer in the memory buffer 29 has been pushed back. The speed at which the audio content is played back as the memory buffer 29 is being backed up, can be fixed or variable, under control of the spectator.

Fast forward—opposite of the rewind function. Can be invoked only when the pointer in the memory buffer 29 has been backed up to some degree.

4. Playing Ancillary Content and Related Functions

In addition to conveying principal video channel content to the spectator, the electronic device 16 is also designed to convey ancillary content. Examples of ancillary content include advertisement content, venue or event related contextual content, on-line shopping options and news, among many others. Both can be in the form of video content, audio content or a combination of video and audio content.

Advertisement content—the advertisement content can be delivered in a wide variety of ways to the spectator. Some examples are discussed below:

The broadcast that is received by the spectator can be provided with an advertisement video channel that can be selected by the spectator in the same manner as he/she selects a principal video channel. For clarity, by principal video channel is meant a video channel that conveys real time video information associated with the live sporting event. Of course there may be more than one advertisement video channel. The channels can be organized in terms of language; for instance, one advertisement video channel in English, one in Spanish and one in French. Alternatively, the channels can be organized in terms of product types or services being promoted.

The advertisement content is embedded in the video content delivered over a principal video channel. The advertisement content can be inserted at the editing stage on the content production console, (see the block diagram in FIG. 1). In this fashion, every spectator receives the same advertisement. The advertisement can be in the form of advertisement clips, such as short movies, banners or graphical elements overlaid on the image or "ticker" type areas running on the screen. It should be appreciated that other ways can also exist for presenting the advertisement video content on the principal video channels without departing from the spirit of the invention.

The advertisement content can also be embedded in the video content delivered over the principal video channel with the insertion occurring at the electronic device 16, rather than at the content production console. Specifically, the advertisement video content is broadcasted over a dedicated channel and instructions are sent to the electronic device 16 that will control when advertisement content from the advertisement channel is injected in a principal video channel. Such instructions will determine when advisement content will start to be played over the principal video channel and the duration of such play. The instructions are interpreted by the software managing the operation of the electronic device 16 to control when to start injecting the advertisement content and when to stop.

Venue or event related contextual information—Venue related contextual information is information that is associated to the venue where the event is held. In the case of a race car event, the venue related contextual information may include:

Map of the venue;
Map of the race track
Information on key locations such as washrooms, vending stands, medical facilities and emergency exits, among others;
History of the venue;
History of the track (if different from the venue)
Schedule of future events to be held at the venue;
Costs schedule for services or products that a spectator may acquire at the venue In a non-limiting embodiment, the electronic device 16 can have GPS receiving capabilities. In such an embodiment, the electronic device 16 is equipped with a GPS receiver (not shown in the drawings), such that the electronic device 16 can obtain location information in the form of GPS coordinates associated with its location. This assumes the GPS receiver has an unobstructed view of the sky to pick up satellite signals. More specifically, these GPS coordinates can be displayed to a spectator on the display screen 802 of the electronic device, in relation to a map of the venue, specifically showing to the spectator its location relative to the map. As such, the spectator will know where he/she is in relation to the layout of the venue.

These GPS coordinates can enable the spectator to locate him/herself in relation to specific facilities at the live sporting event. For example, the transmitter 14 can transmit to the electronic devices 16 in the wireless RF transmission cartographic data. For example, the cartographic data provides a map of the venue and shows the location on some key facilities such as washrooms, food vendors, medical/emergency facilities, exits, etc . . . The electronic device 16 then stores this database in its memory 102, such that it can be easily accessed by the processor 100. As such, when GPS coordinates are produced a portion of the map or the map in its entirety is shown on the display screen 802, depending on the zoom level, identifying the location of the spectator. The locations of these facilities can then also be displayed on the map of the venue along with the GPS coordinates of the spectator. In this manner, the spectator would be able to locate him/herself in relation to these facilities.

The facilities can be displayed on the map of the venue in the form of symbols, or text. Preferably, the symbols or text would be indicative of the service/facility that is located at that area on the map. For example, the medical/emergency facilities may be depicted on the map via a red cross, the washroom facilities may be depicted by a W/C sign, or the traditional man and woman signs ♦ ♦, the food facilities may be depicted by a knife and fork symbol ♦, etc . . . In addition, the location of the electronic device 16 can also be depicted on the map via an icon, such as a star, for example, such that the spectator knows where he/she is in relation to the other facilities depicted on the map. In an alternative embodiment, the position of the electronic device 16 may just be depicted via a flashing dot.

In order to avoid the map being overcrowded with symbols for each of the different facilities available, the spectator could select which facilities to display on the map by a specific type of facility from a menu. For example, if a spectator needs to find the washrooms, they may access the map of the venue and have the icons associated with the washrooms appear on the map, as well as an icon associated with the position of the spectator. In that manner, the spectator will have a clear indication as to where the closest washroom is located.

In yet another possibility, the electronic device 16 may be equipped with software that enables the electronic device 16 to provide the spectator with directions as to how to get to a certain location. For example, based on the GPS coordinates of the electronic device 16, and the GPS coordinates of a selected location stored in the GPS coordinates database, the processor 100 can use the direction software to determine the best route to get from where the spectator currently is, to the desired location. These directions can then be displayed to the spectator on the electronic device 16 screen. The manner in which the spectator requests directions can be done in a variety of ways without departing from the spirit of the invention. In one example, the spectator may simply access a directions menu on the user interface, and select from a list of options such as "directions to the washrooms", "directions to the nearest exit", "directions to the hot dog stand" etc. Alternatively, the spectator could highlight a specific facility icon depicted on the screen via up/down buttons on the keypad, and then hit an "enter" button in order to select that icon. The directions software would then provide directions to the facility associated with the selected icon. The directions provided to the user can be in the form of a text listing the route to follow or in the form of arrows showing a path to follow on the map of the venue.

The electronic device 16 may also enable the spectator to store user-defined GPS coordinates into its memory 102. This may be desirable in the case where the spectator wants to remember specific locations at the venue. For example, in the case where a spectator parks his/her car in the stadium's parking lot, upon exiting the car, the spectator may choose to store the GPS coordinates associated with the location of the car in the memory 102 of the electronic device 16. This could be done by invoking the GPS feature on the user interface, and then selecting a "store coordinates" option from a menu item with the appropriate selection keys. The coordinates could then be confirmed and stored by pressing an "enter" key. Those coordinates can then be associated with any suitable icon displayed on the map, thus allowing the spectator to quickly and conveniently find the location of the car. As such, the spectator enters a command on the user interface of the electronic device 16 to recall the stored location information and show the position on the display with relation to a map of the venue. An advantage of this feature could be that at the end of the live sporting event, when the spectator wants to find his/her car, they would then be able to use the directions feature, as described above, to get directions from their current location, back to the GPS coordinates associated with their car.

Event related contextual information is information relating to the event held at the venue. In the example of a race car event, the following is considered to be event related contextual information:

List of the racing teams;
Profile of individual drivers;
Current standings in the championship;
Information about settings of one or more cars participating in the car race;
Information about the regulations governing the car race The venue or event related contextual information could be delivered to the spectator over a dedicated channel that the spectator can select for viewing at his/her leisure. The channel selection is effected as described earlier. Alternatively, the venue or event related contextual information could be embedded in the video content of a principal video channel.

The ancillary content provided to the spectator over the wireless RF transmission can also include:

News—Relates to different types of news service, such as "breaking news", weather information and economic information, among others. The news information can be delivered to the spectator as in the case of the venue or event related information.

Trivia/Surveys/Games—Provides the spectator with trivia questions, or surveys or games in order to keep the spectator occupied during down-time at the event.

Meteorological/Environmental information—This information would provide the spectator with current weather information and a forecast for future weather conditions. This may be particularly useful at outdoor events where spectators want advance notice if it is going to start raining or snowing. The environmental information may provide the spectator with environmental conditions associated with the live sporting event. For example, in the case of a golf game, the environmental information may include the speed and direction of the wind, the slope of the green, or any other conditions that might affect the game.

Shopping information—Provides the spectator with information allowing the spectator to purchase products or services related to the live sporting event, such as T-shirts, caps, etc.

The electronic device 16 may include a spectator preference profile such that the electronic device 16 provides the spectator with ancillary data according to rules outlined by the spectator. The ancillary data preference profile may be stored in the memory 102 or the storage media reader/writer 106 such that it can be accessed by the processor 100. The preference profile would advise the processor 100 of what ancillary data the spectator is most interested in, and how the spectator would like to have the ancillary data presented. The following is an example of some rules that outline a specific spectator's ancillary data preference profile:

1. Provide a spectator with News information at all times in a ticker type of format at the bottom of the screen
2. Each time the score, or rankings, change, display a screen showing the current standings for 10 seconds.
3. During the idle time in the event or game (such as half time or a football game) display to the spectator any trivia games or spectator surveys.

The software that runs the electronic device 16 includes a module that provides the function of an ancillary data selector. The ancillary data selector decides which type of ancillary data to present to the spectator based on the preference profile. For example, based on the preference profile information, the electronic device 16 will present the ancillary data in the manner outlined in the preference profile.

In this fashion, the spectator is presented with the ancillary data that is the most relevant or of most interest to him/her. The user interface of the electronic device 16 can be designed to allow the spectator to stop the presentation of ancillary data at any time, via menu options presented to the spectator.

5. Profile Based Content Management

The electronic device 16 is designed to implement profile based content management. The memory 102 of the electronic device 16 includes data that defines a profile. On the basis of this data the electronic device 16 can filter the video, audio or data being displayed to the spectator. In one form of implementation, the wireless RF transmission issued by the transmitter 14 conveys generic spectator content that is the same for a group of electronic devices 16 or for all the electronic devices 16 that receive the wireless RF transmission. The spectator profile in one or more of the electronic devices 16 filters the generic content to create a spectator specific content. The spectator specific content can differ from the spectator generic content in many possible ways. For example, the spectator profile is set to prevent access to certain content in the generic spectator content. In another example, the spectator profile changes the way the content in the generic spectator content is presented to the spectator. Several possibilities are discussed below in greater detail.

In a specific example, the profile defines a spectator category among several possible spectator categories. For instance the profile may allow for gender-based classification, such as male and female. In another possibility the profile is designed such as to create age-based classification. Yet another possibility is to create revenue-based classification where spectators are classified according to the amount of personal income. Another possible option is to define a profile based on personal preferences, such as:

My preferred racing team;
The type of food preferred;
Type of automobiles the spectator is interested in;

The profile data loaded in the memory 102 via the graphical and navigational layer. The spectator is presented with an information screen inviting the spectator to answer questions that will define the profile. The number of questions necessary to define the profile can be minimal, such as requiring the spectator to specify "male" or "female" or larger in the case of more complex profile structures.

The profile can be designed to be defined only once or it can be updated over time. Simple profile structures such as gender-based ones will need to be defined only once and as long as the same spectator keeps the electronic device 16 no change will be required. More complex profile structures may need adaptation more often. Profiles based on spectator choices will likely change to reflect the spectator's changing preferences over time. In the case of sophisticated spectator profiles, for instance those that factor events or conditions occurring at specific auto racing events, the profile will need to be updated by the spectator at each particular event.

Based on these spectator profiles, the advertisement that is conveyed to the spectator can be oriented towards their specific profiles or interests. Likewise, the type of merchandise that is presented most prominently in the shopping catalogue can also be geared towards a spectator's specific profile.

Content management based on spectator profile implies handling the content differently depending on the data in the profile. The reader will appreciate that a wide variety of options exist. The following specific examples illustrate the concept:

- The profile in the electronic device 16 is defined on the basis of age group. Three age classes exist: (1) up to 25 years old; (2) from 26 to 60 years old and (3) from 61 and above. The advertisement content is structured according to the age based classification. Specifically, the advertisement content includes three streams, each tailored to a specific age group. When an advertisement is to be played, the spectator only sees the stream that corresponds to the profile data stored in the memory 102. In addition, the products featured most prominently in the shopping catalogue may also be structured according to the age based classification. For example, for the first age class, T-shirts and hats may be featured most prominently, while for the second age group, more expensive items, such as signed collector's items, may be featured most prominently.

- The profile in the electronic device 16 is defined on the basis of amount of venue or event contextual information the spectator would like to receive. Say the profile allows for two levels of information, one being low and one high. The venue or event contextual information that is sent to the electronic device 16 is structured as independent streams, one containing more information than the other such that the stream presented to the spectator is the one that matches the profile data stored in the memory 102.

- The profile in the electronic device 16 is based on racing teams the spectator is most interested in. For example, the profile allows the spectator to specify three teams of interest in the order of preference, such as team A, team B and team C. The video feeds that are broadcasted to the electronic device 16 include views from cameras in all the racing vehicles. The profile data based on team preference will allow the spectator to define an order of preference in which the video feeds will appear on the screen of the electronic device 16 when the spectator switches "channels". For instance the default view will be the video feed from the vehicle camera of team A. When the spectator switches to another video feed, the video feed that appears on the screen of the electronic device 16 is the one from team B. The next view will be the one from team C.

- Service level profile. This profile will allow the spectator to access only the services that the spectator paid for. For example, the spectator may have opted to access the financial news service during the live sporting event and paid a premium for this service. The spectator profile data in the memory 102 of the electronic device 16 reflects this choice and enables the electronic device 16 to deliver the financial news service for viewing on the screen. When a service level profile is used it is preferred to design the spectator profile structure that is stored in the memory 102 of the electronic device 16 in a manner such that the spectator cannot freely change the service level portion of the profile. The service level portion of the profile can be altered remotely, such as for example by sending along with the authentication information used to unlock the electronic devices 16, data indicating which service level is associated with a particular electronic device 16. Specifically, this can be done by broadcasting the block of identifiers and sending with each identifier a code identifying the service level for the electronic device 16 associated with the identifier. When the electronic device 16 unlocks itself by matching an identifier being broadcast to its own identifier, it reads the service level identification code and stores it as spectator profile data in the memory 102. At this point, the spectator profile data will dictate which service the spectator can access and which service is blocked.

The manner in which the data in the profile stored in the memory 102 manages the content delivered to the electronic device 16 can vary and many implementations are possible. The profile data is a data structure and that data structure is associated with the structure of the content delivered to the electronic device 16 to effect the content management. In this type of implementation, the content is structured as a collection of individual components that can be handled as per the data in the profile. In the case of the first example, where the profile is based on age groups, the advertisement content is conveyed as three separate streams, and depending on the data stored in the profile only the respective stream will be displayed. In the second example, the event or venue contextual information is conveyed as two separate streams, one stream containing more information than the other.

FIGS. 7 to 18 are more detailed examples of the operation of the electronic device 16, showing in particular menu possibilities and different types of information that can be delivered. It should be expressly noted that the above are merely examples that should not be used to limit the scope of the present invention.

Figure 8:
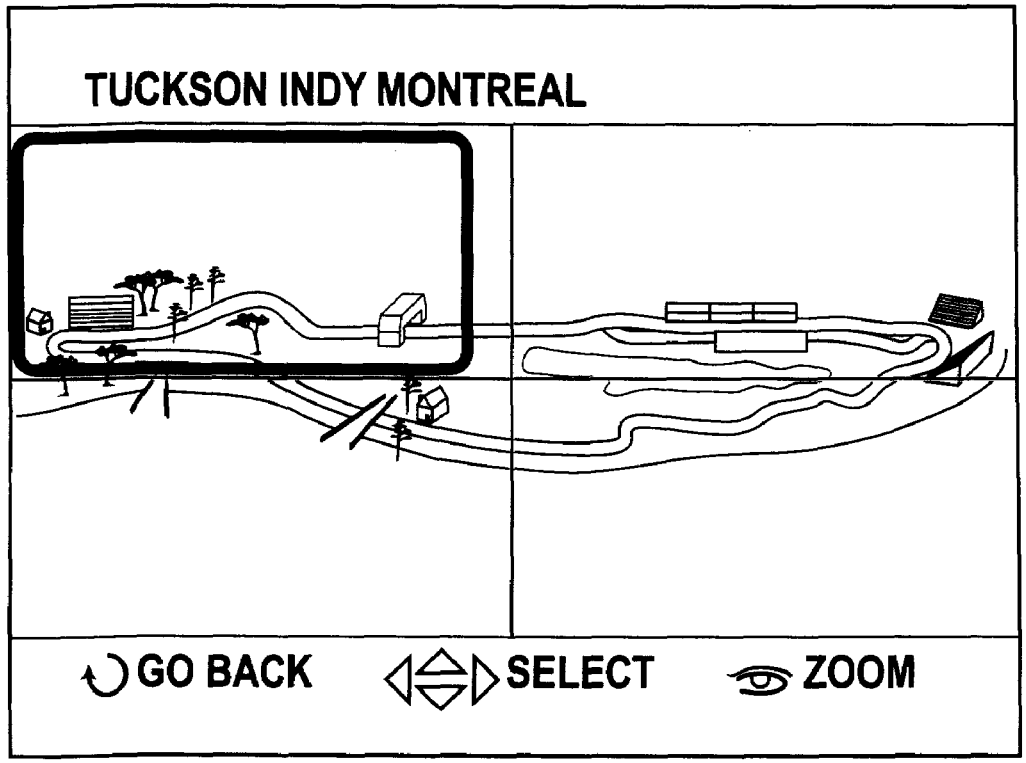
Figure 9:
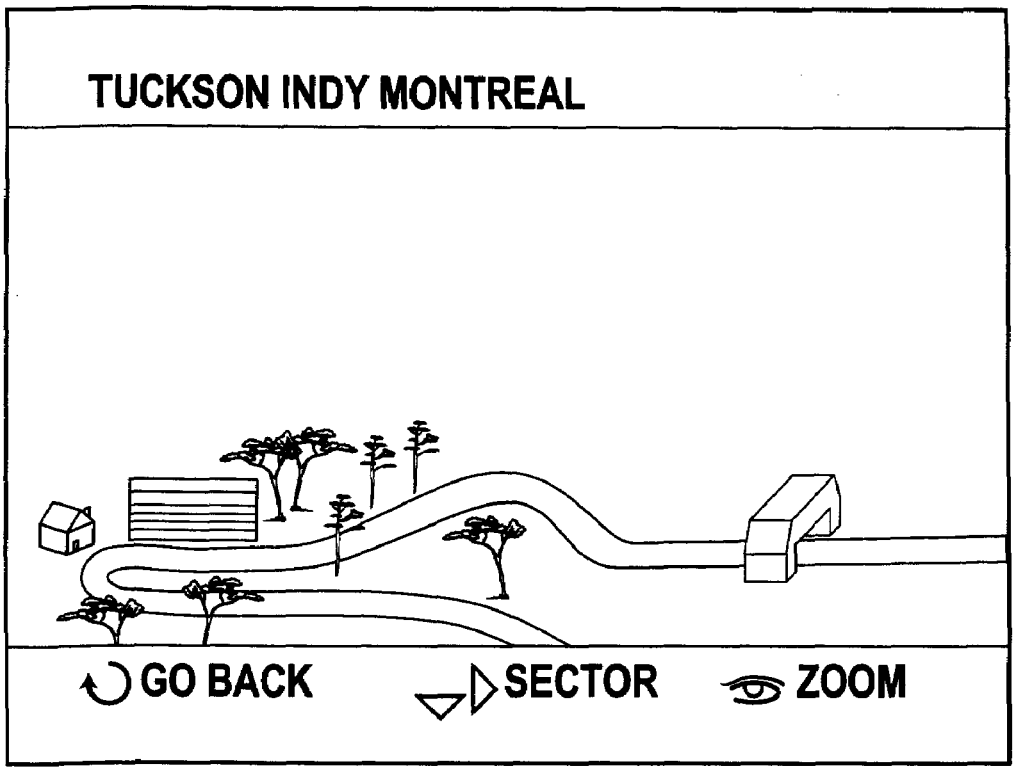
Figure 12:
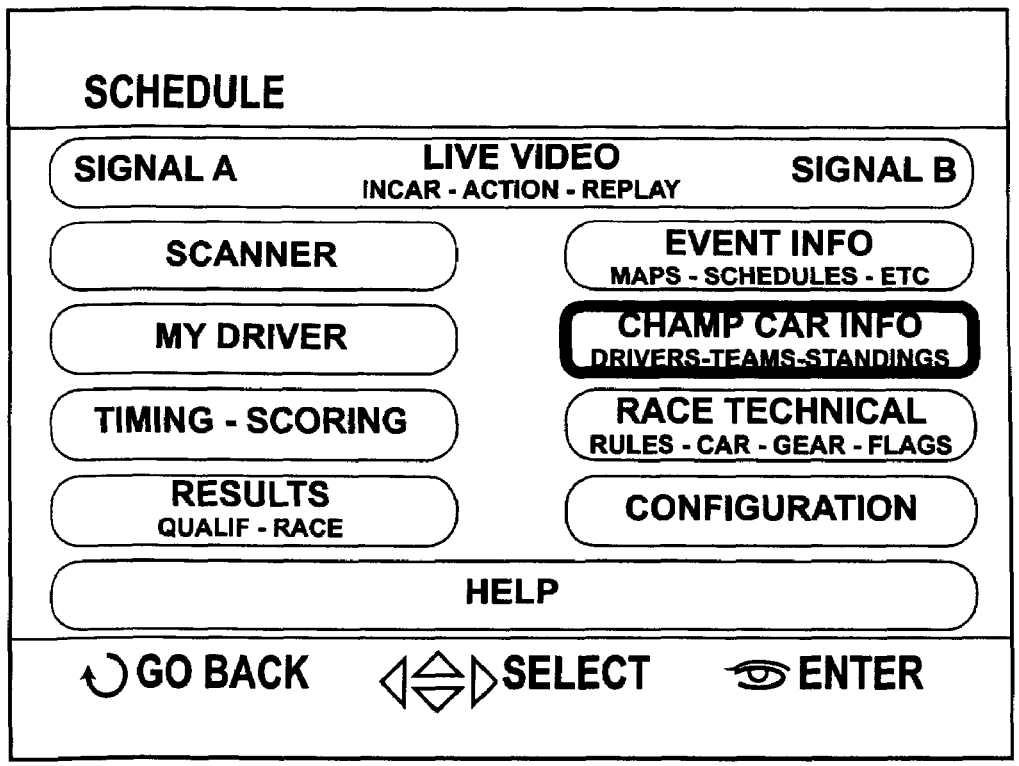

FIG. 12 is a root menu page allowing the spectator to access different types of functions and content of the electronic device 16. Specifically, the spectator can select at the top of the screen the "live video" option that leads to a set of live video channels. Below this option are other options, some of which will de detailed:

- Scanner—allowing access to the independent audio feeds, such as radio traffic between drivers and teams, audio commentary, etc.
- Timing and scoring—this option page is selected from the page at FIG. 12. The timing and scoring page provides information of the type shown in the drawing such as best lap, lag, etc. Additional information may also include number of laps completed, number of laps to go, among others;
- Results—allowing access to a results page;
- Event info—by selecting this option the spectator accesses a sub-menu shown in FIG. 7. The sub-menu has a number of options, some of which will be described below:
    - Site—shows a map of the venue, as seen in FIG. 8. The spectator has the option to zoom on different sections of the map. The map is divided in quadrants and the each can be highlighted. Currently, the upper left quadrant is highlighted. By selecting the highlighted quadrant the zoom function is enabled for that quadrant, as shown at FIG. 9.

Figure 11:
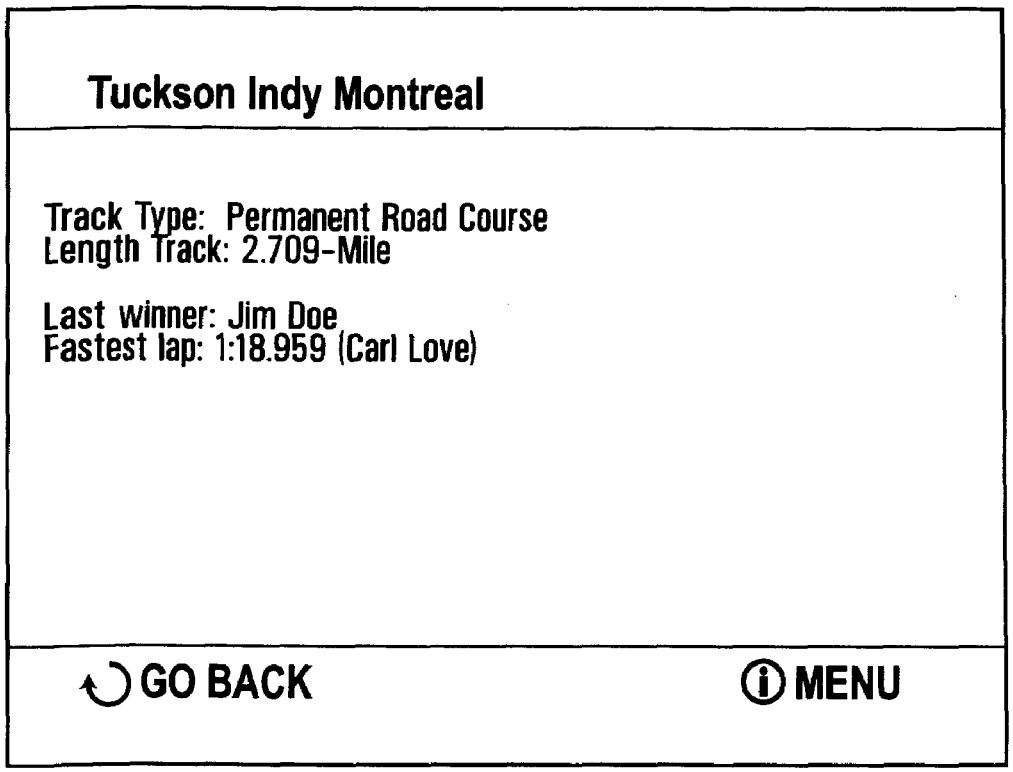

Track—shows info regarding the track, as seen in FIG. 11.

Figure 10:
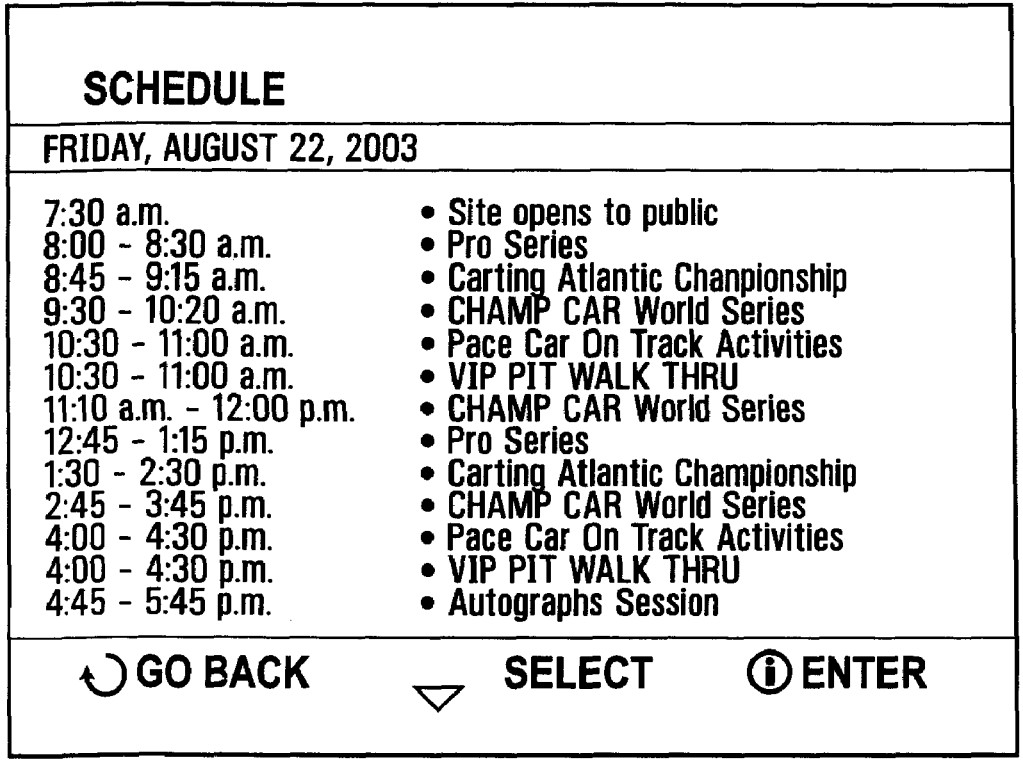

Schedule—shows schedule information, as seen in FIG. 10.

Figures 13, 14:

Champ car info—referring back to FIG. 12, by selecting this option the spectator accesses a sub-menu. The sub-menu has a number of options, some of which will be described below:

Drivers—by selecting this option the spectator has access to a list of drivers as shown at FIG. 13. By highlighting and selecting a driver in the list the spectator can access a detailed page of that particular driver, as seen for example at FIG. 14.

Standings—by selecting this option the spectator has access to a current standings list, as shown at FIG. 15;

Teams—by selecting this option the spectator has access to a list of the teams participating at the event, as shown at FIG. 16. The spectator has the option to highlight a particular team in the list and access a more detailed page showing additional information on the selected team.

Figures 17, 18:
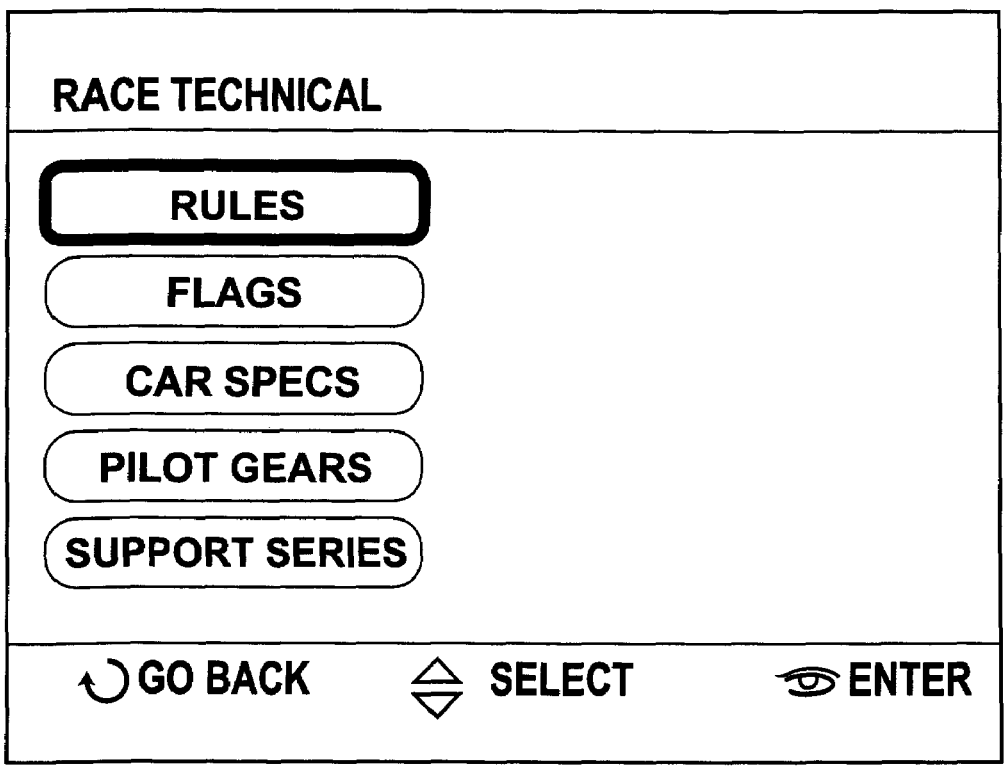

Race technical—referring back to FIG. 12, by selecting this option the spectator accesses a sub-menu shown at FIG. 17, providing information about the race.

6. Automatic/forced Video Switching

In one embodiment the electronic device 16 is designed such as to provide automatic video channel sequencing such as to present to the spectator a perspective of the event that is of most interest to the spectator. For example, the spectator may wish to visually follow a particular car on the track. Without any automation, the spectator is required to manually switch video channels such as to keep the car of interest always in view. This may not be optimal for obvious reasons. The electronic device 16 under the present invention provides a mechanism allowing to automatically sequence through the video channels such as tracking a moving object, such as a vehicle on the race track. Several options to implement this feature exist. Examples are discussed below:

Video channel switching based on commands in the wireless RF transmission—the content production team determines, for each car, what is the optimal viewing channel at any given moment. This can be done manually or automatically. Video channel switching commands are then sent to the individual electronic devices 16 in the wireless RF transmission. For example, for a given car, say car A the data being sent to the electronic devices 16 contains a field that specifies the video channel that provides the optimal viewing. The information in this field is updated continuously as the car moves on the track. If automatic sequencing is enabled at the electronic device 16, the electronic device 16 will show on the display screen 802 the video channel that is being specified in the data field. The software running the electronic device 16 is continuously looking for the video channels switching commands in the wireless RF transmission and when those commands are observed the display is switched to the new video channel.

Video channel switching based on car displacement information (speed information). The electronic device 16 receives data contained in the wireless RF transmission that defines a group of video channels for use in automatic sequencing. The data will specify the following parameters that are determined before the car race starts:

Which are the channels to use for sequencing, say channel A, channel B and channel C;

The sequence—switch from channel A to channel B and then to channel C and then start again;

The field of view of each channel, the field of view being expressed in terms of track distance. For example, channel A's field of view is of 5 km of track distance, channel B's field of view is of 7 km of track distance and channel C's field of view is of 9 km of track distance.

The spectator at the electronic device 16 starts watching the event and sees a car that the spectator would like to track automatically. The spectator specifies (via menu selection or other the car to track), waits until the car is in the field of view of any of the channels A, B or C and then activates the automatic tracking feature. The automatic tracking feature invokes a car tracking software that uses an algorithm that will read the speed of the car that was specified by the real time data that is continuously broadcasted and determine based on a simple speed versus distance computation, the time when the car will exit the field of view of the currently watched channel. Specifically, in the case of channel C, the algorithm computes the time required for the car to travel 9 km which is the field of view of the channel. After this computation is completed, an internal clock is started. When the time interval elapses, the algorithm issues video channel switching command to switch video channels automatically according to the switching order specified. The same operation is repeated continuously. Assuming that the speed of the car is reported with a reasonable accuracy, the timing of the video channels switching events can be dynamically controlled such that to maintain the car always in view for the spectator.

Video channel switching based on car displacement information (position coordinates information). This approach is somewhat similar to the example above except that the video channel switching is effected on the basis of coordinates of the car reported in the real-time data being broadcast. Specifically, the coordinates information can be obtained from a Global Positioning System (GPS) in each car, delivered to the head end 12 and then broadcast in the wireless RF transmission to each electronic device 16. The video channels in the sequencing group are characterized by a field of view covering a range of coordinates. The spectator simply specifies the car to be tracked. On the basis of the coordinates of the car of interest, the algorithm determines in which video channel coordinates range the car is located and then switches to that channel automatically. At each coordinate update received in the wireless RF transmission, the same operation is performed and if the car is now in the field of view of a different channel then the algorithm performs the switching accordingly.

In another embodiment the electronic device 16 is designed such as to provide a forced video channel switching when an important event develops on the race track. For example, if an accident occurs the spectators of the electronic devices 16 are likely to be interested to switch immediately to the video channel that conveys images of the accident. This process can be facilitated by introducing in the wireless RF transmission a flag to designate the video channel that will show the best possible angle of such priority event. Typically the technician at the content production station 20 will identify the video channel that best shows the action and will introduce in the wireless RF transmission a flag which will mark the channel. The flag can be any type of data. For instance the flag can be the channel identifier. When the electronic device 16 receives the flag, the software interprets it and it causes the display to automatically switch to the video channel designated. If desired, a feature can be provided to allow this automatic video channel switching to be disabled, in the case the spectator is not interested by this feature.

Yet, in another possible variant, the automatic video switching is effected on a basis of a certain characteristic associated with the competition, such as for instance, a particular position of a participant in the event. For example, the position can be the lead position, thus causing the electronic device 16 to automatically switch video channels to show continuously the leader of the race. As with the previous example, the technician at the head end 12 manually or with the assistance of automated tools identifies which video channel best shows the leader of the race and inserts a suitable flag in the wireless RF transmission. The electronic device 16 is programmed in turn to play the video channel that is associated with the flag. Therefore, when the flag changes, in other words it is shifted from one video channel to the other, the electronic device 16 will switch on the display screen 802 video channels accordingly.

Figure 19:
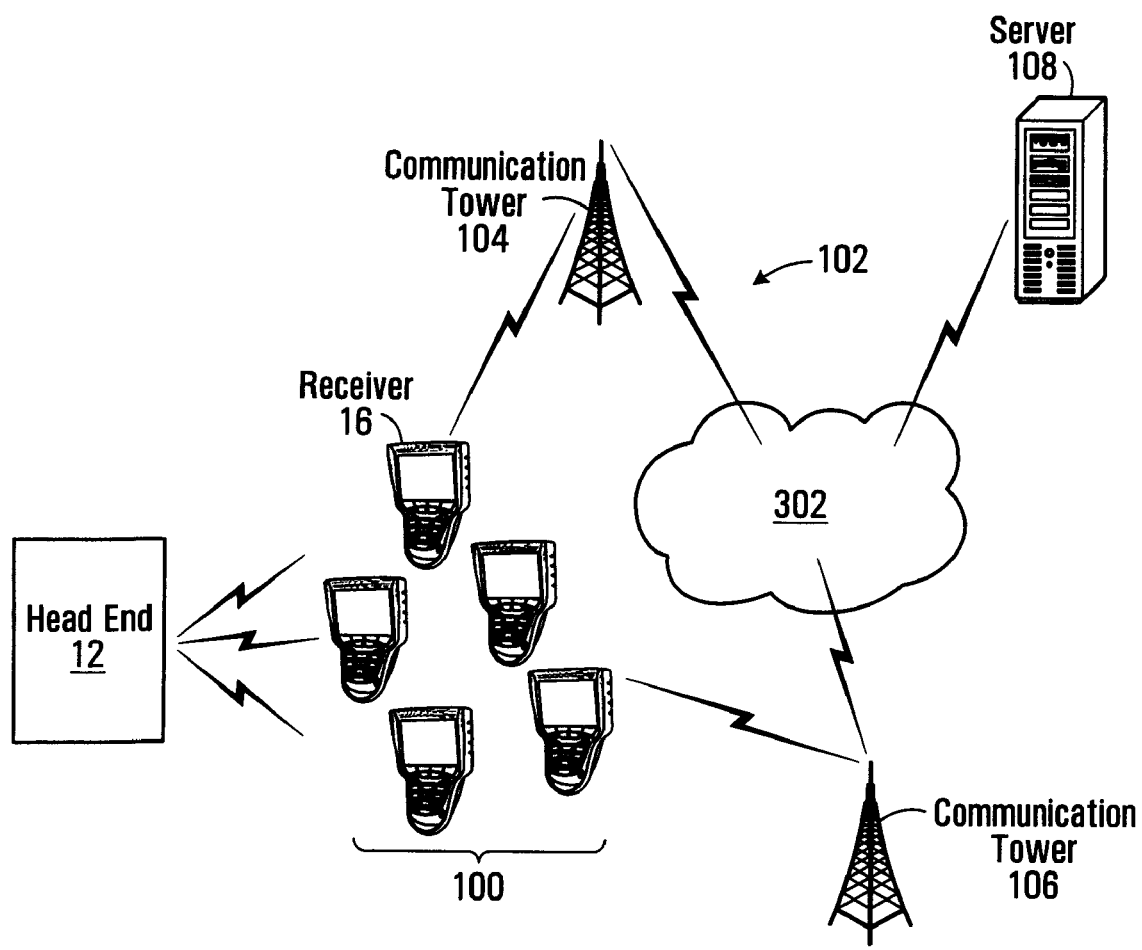
FIG. 19 is diagram of a variant of the system where the individual handheld electronic devices are provided with a bidirectional communication capability.

In another possible variant, the electronic device 16 has bidirectional wireless communication capabilities. Therefore, the electronic device 16 can receive information wirelessly and also send information wirelessly. FIG. 19 illustrates a bidirectional communication system according to a non-limiting example of implementation.

Assume for the sake of this example that a set 100 of electronic devices 16 are located at a live sporting event, say a car race. The electronic devices 16 all receive the wireless RF transmission from the head end 12. The electronic devices 16 can also communicate individually with a remote entity via a cellular network 102. In this example, the cellular network 102 has two cellular towers 104 and 106 located away from one another such as to provide adequate reception coverage from anyone of the electronic devices 16 at the live sporting event. Each electronic device 16 is provided with the functionality allowing it to establish communication over the air interface with the cellular network 102. This functionality includes a transmitter and a receiver sections that can communicate in the same manner as a cellular telephone. Since this technology is generally well understood it will not be described here. Another possibility that can be used instead of a cellular network is a WiFi network or any other cellular type infrastructure allowing individual wireless communication to take place between each electronic device 16 and a remote entity.

It is not necessary, nor even preferred to provide the communication channels from the electronic devices 16 toward the cellular network 102 with the same bandwidth as the bandwidth of the link between the head end 12 and the handheld electronic devices 16. In practice, the amount of information that needs to be sent from the individual handheld electronic devices 16 is small and does not require the amount of data carrying capacity the wireless RF transmission from the head end 12 needs.

7. On-line Shopping and Games

The wireless bidirectional communication capability allows providing increased interactivity for the spectator and thus enhancing it entertainment experience. Specific examples will be discussed below.

Online shopping over the electronic device 16—The concept of delivering to the electronic device 16 an electronic catalog was discussed previously. The availability of a bidirectional communication allows the spectator to select merchandise to purchase and electronically complete an online purchase. Assume for the sake of this example that the spectator wishes to access the on-line shopping information such as the electronic catalog in order to make a purchase of a souvenir, say a T-shirt with the logo of his/her favorite racing team. The electronic catalog having been loaded previously, as it was described earlier, the spectator accesses the catalog via the user interface 800. This may be done by pressing one or more dedicated buttons on the spectator interface 800 or via a menu item on the GUI of the electronic device 16. Once the electronic catalog has been accessed, the spectator navigates to the desired item by buttons on the user interface 800. At that point the spectator makes the selection and proceeds to a checkout page. The checkout process can be designed in a number of different ways. The first possibility is to require the spectator to enter the necessary information such that the on-line transaction can be completed. This information includes, his/her name, payment instrument such as credit card details, shipping address information, among others. This information is entered by the spectator by using buttons on the user interface 800. Note that the example of the user interface shown in FIG. 3 would require to be expanded to include the necessary alphanumeric characters to allow such data entry to be made. After completion of all the fields on the checkout page the electronic device 16 communicates over the cellular network 102 with a remote server 108 to complete the transaction. The session would include transmitting to the server 108 the information contained in the checkout page, such as the article or service to be purchased, the payment information and shipping address information. At this point the transaction is completed and the spectator will receive its merchandise via the selected delivery method. Another possibility to effect the on-line transaction is to store on the server 108 (or any other network server that communicates with the server 108) the necessary information on the spectator such as to avoid having the spectator enter the data via the electronic device 16. This possibility is discussed in greater detail in connection with FIG. 21. Specifically, the server 108 contains user records associated with different spectators, where each user record includes an identifier for authentication purposes, payment instrument for on-line transactions, shipping address, etc. In such case, the checkout process would involve sending over the cellular network 102 the identification of the article or service the spectator wants to purchase and the spectator identifier to allow the server 108 to retrieve the correct user record. The second possibility is arguably more practical because it avoids the necessity of typing on the user interface 800 a lot of information.

Figure 20:
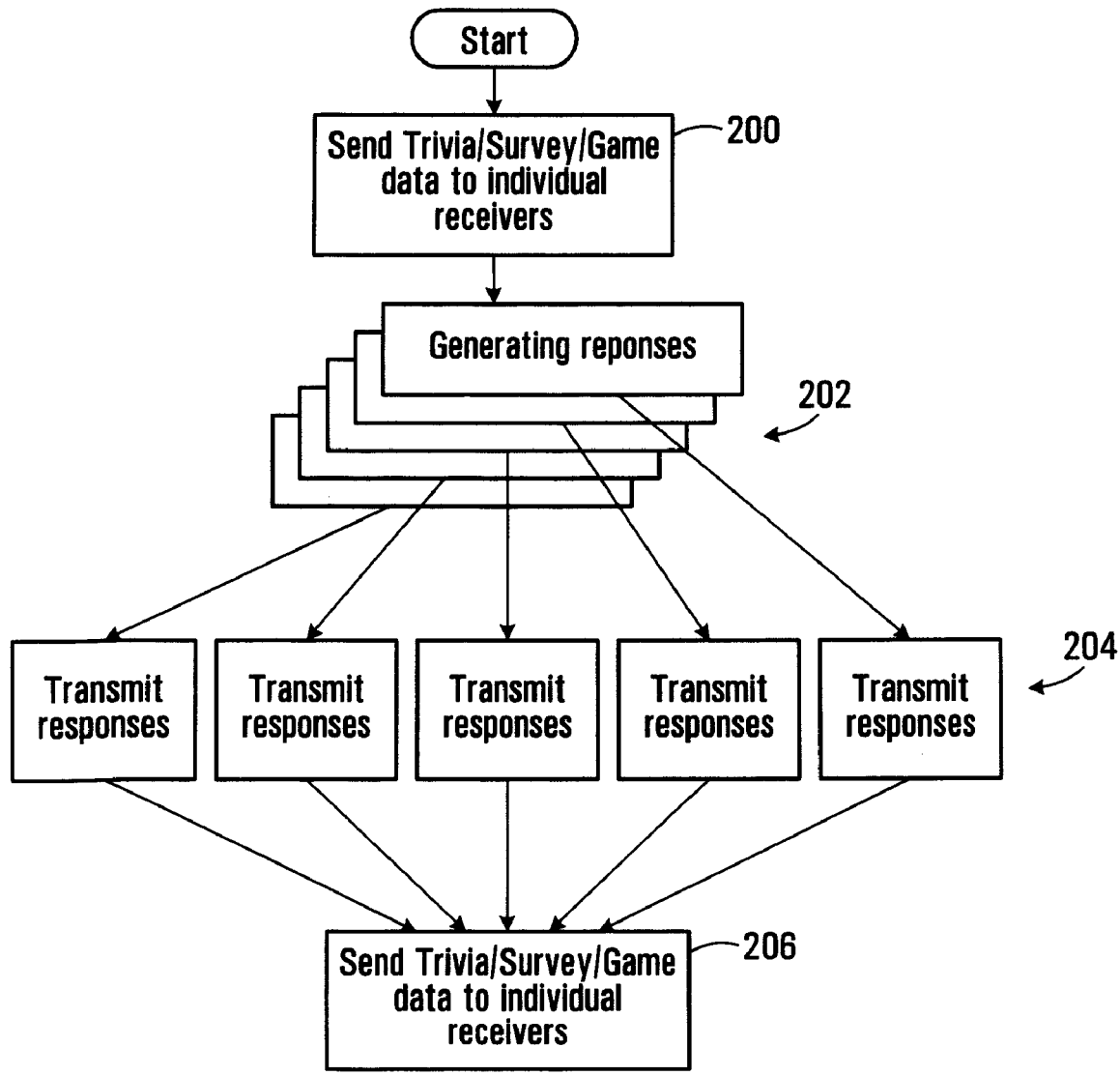
FIG. 20 is a flowchart of a process for managing trivia/survey/game data.

Trivia/Survey/Games. This option was discussed earlier in connection with the embodiment having a unidirectional communication capability. The bidirectional communication can significantly enhance the interactivity of the spectator's experience. Several examples can be provided to illustrate this. In a first example, the spectator is presented with a trivia game that includes a number of questions associated with the live sporting event or a participant of the event. The questions are shown on the display of the handheld electronic device 16 and they are extracted from data that is transported in the wireless RF transmission. The spectator may answer selections by operating buttons on the user interface 800. There may be a series of questions or a single one. The answers are collected and when all the questions have been answered the answers are sent to the server 108. The process is illustrated by the flowchart on FIG. 20. Step 200 shows the process of embedding the data necessary to generate the trivia game questions in the wireless RF transmission. This is done by the head end 12. The data can be stored in the database 602. At step 202 the individual electronic devices 16 receive the data, generate the questions on the display and the spectators enter responses in the respective electronic devices 16. Multiple blocks are shown for step 202 to indicate that multiple electronic devices 16 are involved in the process. At step 204 each individual electronic device 16 sends the responses to the server 108 over the cellular network 102. At step 206 the server 108 processes the responses and then takes some type of action on the basis of the processing. The type of action that can be selected depends on the particular game strategy. Examples include:

Forwarding to each electronic device 16 information indicating the correctness of the responses. Such information is conveyed over the cellular network 102. This approach allows conveying to each spectator a personalized message, such as his/her score.

Compiling the responses from individual electronic devices 16 and ranking the participants in terms of score. The score is sent to the individual electronic devices 16 over the cellular network 102. Therefore, a electronic device 16 can receive the list of highest ranking participants, such as the top 10 participants;

Awarding a prize for the highest score and notifying the particular electronic device 16 of the win;

Using the wireless RF transmission to send the information on the basis of the processing to the electronic devices 16. This approach does not allow a personalized message but can still be used to present to spectators information on the trivia/survey, such as for example, the list of highest ranking participants and/ or the correct answers to trivia questions or in the case of a survey the compiled results of the survey.

Another possibility is to tie the trivia or survey questions to action occurring at the live sporting event. For example;

In the case of a car race when an accident occurs, a question is sent to each electronic device 16 identifying the participants involved and asking who is at fault;

In the case of a hockey/football or soccer game asking a question as to whether the call of the referee is correct. For instance in the case of a hockey game, when a player is given a penalty, the question asks if the penalty call was correct. In this fashion, the spectators that have the electronic devices 16 can vote on referee calls during the actual game.

In the case of a hockey/football/soccer game asking at the end of the game or at the end of a period to identify the player that played the best or was the most useful to his team during the game/period. In this fashion, the spectators that have the electronic devices 16 can vote on player's behavior or performance during the actual game.

The results of the processing of the responses received by the server 108 can be handled as discussed, earlier, in other words, a feedback is provided to the individual electronic devices 16 either via the cellular network 102 or the wireless RF transmission. Yet another option is to publicly announce or display results. In the case of live sporting events held in a stadium or a similar infrastructure that usually has some type of large display screen, the results of the processing can be displayed on the large screen for everyone to see. For example, the message displayed may say that the survey indicates the call of the referee is wrong or that the best player for the period is player X.

The information that is to be displayed on the screen or otherwise announced to the audience can be generated from the server 108 and sent to the display apparatus in any suitable way. The transmission can be wireless or wire line in the case the server 108 is local to the display.

The electronic device 16 can also be provided with a game play functionality that does not require a bidirectional communication. Several examples can be provided to illustrate this variant. For instance, the wireless RF transmission can be designed as a vehicle to convey data that enables the electronic device 16 to acquire game play functionality. Specifically, the head end 12 can be designed to generate video game data which is carried by the wireless RF transmission and received by the individual electronic devices 16. The video game data contains program code for execution by the processor 100 to enable the spectator to play a video game on the display screen 802. The video game that is used for the entertainment of the spectator has images that can be manipulated on the display screen 802. The video game is controlled via the user interface 800. The various buttons of the user interface are assigned functions for interacting with and manipulating the images on the display screen 802.

Another option is to pre-load in the electronic device 16 the video game data and only send via the wireless RF transmission data that will enable the game play functionality by "unlocking" the execution of the video game data. In other words, the spectator is normally prevented from playing the video game, unless the data to unlock the game is received via the wireless RF transmission.

The above discussed options are not strictly limited to video games and can be extended to trivia games/surveys etc. In other words, the game can be loaded or enabled by the wireless RF transmission, as described earlier. When the electronic device 16 is provided with a bidirectional communication functionality, the responses to the game questions, survey or voting can be output as discussed above.

It is also possible to time the game play functionality according to the evolution of the live sporting event. For instance the game play functionality of the electronic devices 16 can be enabled only when a predetermined event occurs during the live sporting event. One such event is a pause during which the action is stopped.

Figure 21:
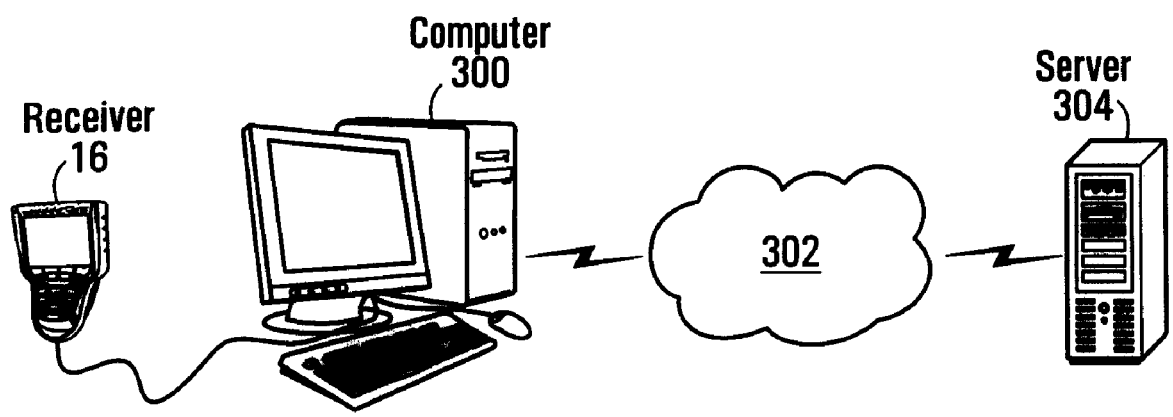
FIG. 21 is a block diagram of a system for performing online service purchase and handheld electronic device management.

Another non-limiting example of implementation of the invention is shown at FIG. 21. In this example the individual electronic devices 16 can be set up for an upcoming event before the event occurs such that the electronic device 16, at the event site, is already programmed and contains the event specific information. After the user purchases the electronic device 16 the user sets a user account, typically with the business organization that delivers the service during live sporting events.

8. Online Service Purchase

The electronic device 16 is connected to the Personal Computer (PC) 300 of the user via the USB port 104 that connects to the electronic device interface of the PC 300. The electronic device interface of the PC 300 can be a USB port on the PC 300. The diagram at FIG. 21 assumes the PC 300 can communicate over the Internet 302 with a server 304. The PC 300 has a data network interface allowing data communication to take place over the data network 302 which in this example is the Internet. In a specific and non-limiting example of implementation the data network interface is an Ethernet connection. The PC 300 has a user interface allowing the user to receive information from the PC 300 and to input information in the PC 300. The user interface includes a keyboard, a display screen and a pointing device. Evidently other forms of user interface can be utilized without departing from the spirit of the invention. The PC is also provided with a processor and a memory in which is stored program data for execution by the processor. As indicated earlier, the PC is connected over the Internet 302 or any other network with the server 304. The server 304 has a computing platform (not shown) having a processor and memory, the processor executing software that implements the functionality of the server 304. To enable data communication between the computing platform and the data network 302, the server 304 is provided with a data communication interface (not shown) that is under the control of the computing platform. The computing platform directs the exchange of information with the PC 300 via the data communication interface.

After the connections have all been established, the server 304 sends to the PC 300 data that in conjunction with the program data executed by the processor presents to the user information via the user interface allowing the user to electronically purchase and specify services to be delivered to the electronic device 16. From the user's perspective, the user is directed to a web site (hosted by the server 304) and presented with a screen of the type shown in FIG. 22. The web site allows the user to set up an account, manage a personal profile and purchase the delivery of services to the electronic device 16 for one or more live sporting events. Assume for the sake of this example that the user must create a new account with the server 304. At this end the user is prompted by the PC 300 in response to data sent by the server 304 to select account identification information allowing him/her to securely access the account. The account identification information can be a user name 308 and a password 310. Once the user name 308 and the password 310 have been selected or accepted by the user in the case they are automatically generated by the server 304, they will be required by the server 304 to allow the user to access again his/her account.

Next, the user is requested to provide personal information such as:

Name 312;

Address 314;

Payment instrument 316 such as a credit card number and expiration date and possibly a security code. The payment instrument 316 is used to pay for the service delivered to the electronic device 16 during the live sporting event and also to pay for merchandise purchased during the live sporting event, as previously described.

Shipping address information 317 for on-line shopping. The shipping address is the address at which merchandise purchased by the user, as described previously, will be shipped;

Language in which the on-line account is to be set.

In addition to the information provided by the user an electronic exchange of information takes place between the electronic device 16 and the server 304. The electronic exchange of information includes the transfer to the server 304 of the unique electronic identifier of the electronic device 16. Such electronic identifier was discussed previously and it is in the form of a hard coded identifier. In this example the identifier is submitted to the PC 300 when the electronic device 16 is connected to it via the USB interface 104 and it is automatically sent to the server 304. Note that the PC 300 may require the use of software that will be able to communicate with the electronic device 16 such as to extract the hard coded identifier from it and transfer it to the server 304 when the user is creating or accessing his record.

The record that is created at the server 304 has three elements of information that allow distinguish it from other records. Those elements of information are (1) the user name; (2) the password and (3) the identifier of the electronic device 16 associated with that user name and password. Note that a possibility exists to assign more than one electronic device 16 with a given record or account.

The next step in the creation of the account is for the user to specify certain preferences that will allow tailoring the service according to personal choices. The page at FIG. 22 has an "Options" button 315 that when "clicked" directs the user to the "Options" page shown at FIG. 23. At that page, the user can specify advertisement options 318 such whether advertisement is desired or not, the type of advertisement to be delivered, namely the nature of the products and services of interest to the user. In a simple case, the user can enter a gender such that the advertisement will be tailored accordingly. In a more detailed example, the user can specify a level or revenue, level of education, subjects of interests, geographical location and language, among others. That information can then be used to build a filter allowing tailoring the advertisement information to be delivered to the user. In a non-limiting example of implementation, the filter is built by the server 304 and uploaded to the electronic device 16 via the PC 300. The filter is in the form of a file that resides on the electronic device 16 and when the advertisement information is received in the wireless RF transmission during the live sporting event the filter will condition what information is to be delivered to the user. The filter can block certain advertisements, select a language in which the advertisement will be delivered, etc.

Figure 23:
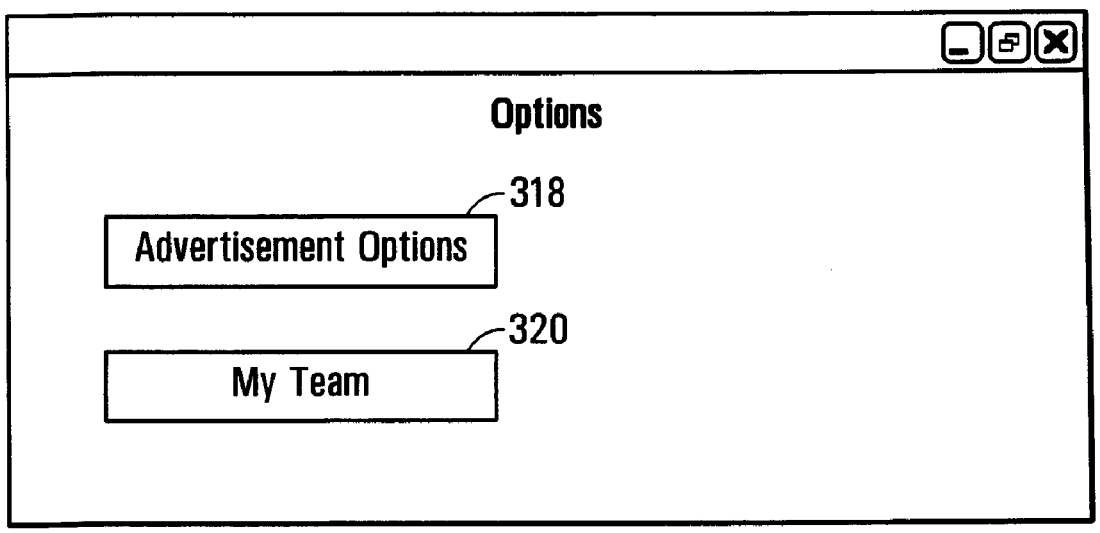

In a possible variant, the user can specify other preferences that relate to information received during the event that is other than advertisement. For instance, the user can specify preferred teams or players to allow delivering information to the user during the live sporting event in a way that is consistent with those preferences. FIG. 23 shows a button 320 "My team" that allows access to a different page (not shown) where those preferences can be specified. That information is then used by the server 304 to build another filter to be stored on the electronic device 16 that will condition the information received during the live sporting event. One specific example of such conditioning is the order in which information on the teams or players is presented to the user. The menu of choices that provides more detailed info on the teams or players is altered on the basis of the filter such that the teams or players that have been specified as being preferred will be given a higher order of priority than teams or players that are less preferred. In this fashion the preferred teams or players will appear first, followed by those that are not indicated as preferred.

Figure 22:
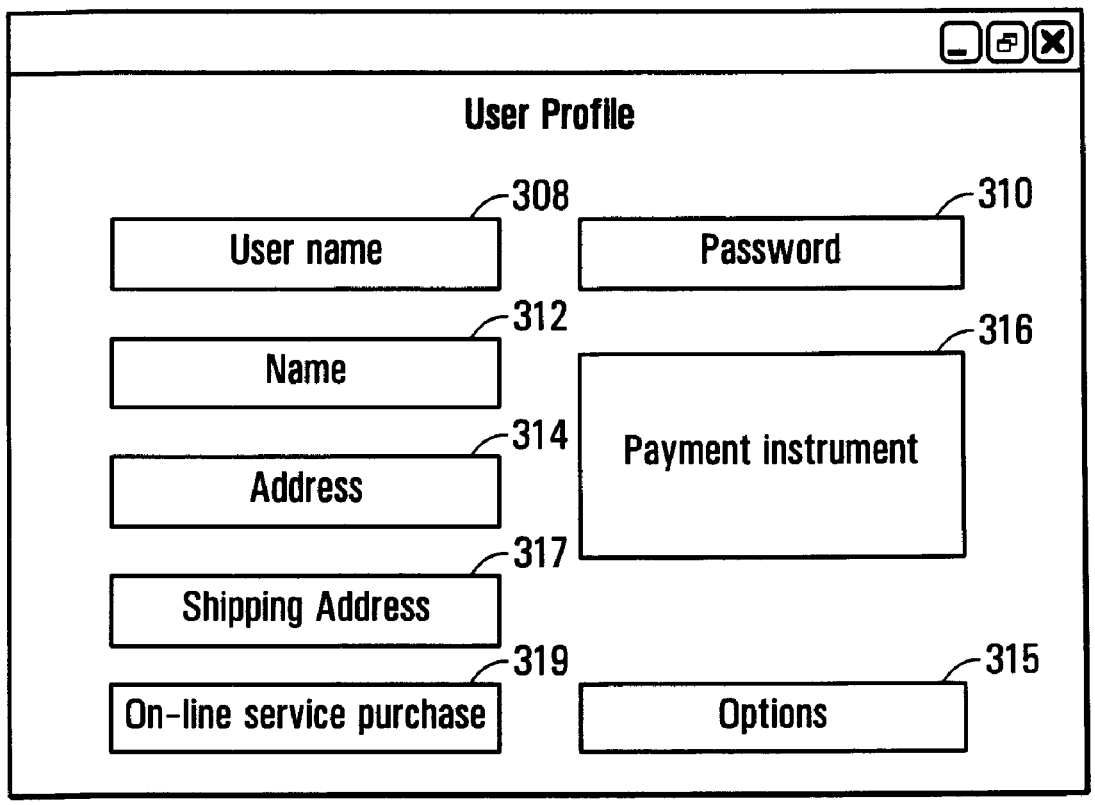
FIGS. 22 to 24 illustrate dialog boxes of a user interface allowing the spectator to enter information for performing on-line service purchases and handheld electronic device management.
Figure 24:
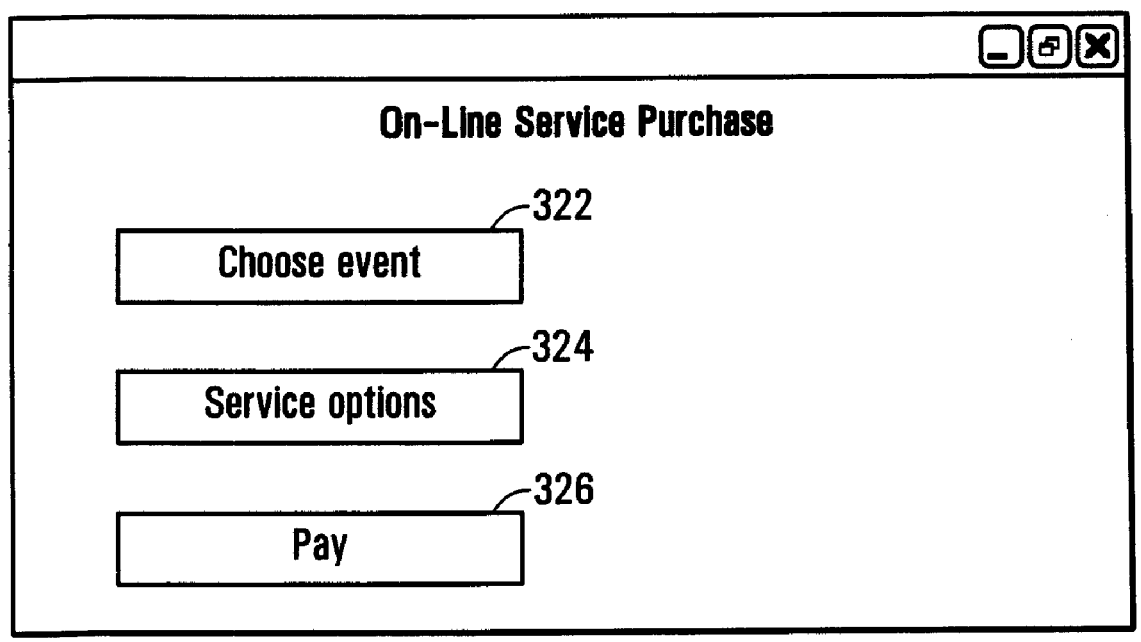

Once the entries on the options page at FIG. 23 have been completed, the user reverts back to FIG. 22 and presses the "on-line service purchase" button 319 that brings the user to the on-line service purchase page at FIG. 24. Here, the user will be requested to authenticate itself to enable the online purchase of delivery of service. The authentication prompt appears on the PC 300 in response to an authentication request data issued by the server 304. The user then enters the authentication information, such as the user name and password, which are transmitted to the server 304 for validation.

If the authentication data is genuine and accepted by the server 304, the user is then directed to a web page allowing the user to select the live sporting event for which content delivery is desired and also to tailor the content to be dispensed depending on the user's tastes and budget. For example, the server 304 sends data to the PC 300 for causing the PC 300 to show a control 322 allowing the user to select the event for which the service is to be purchased. The control 322 can be any suitable control such as for instance a drop down menu box that provides the list of all the events for which service can be purchased.

Once a particular event has been selected, then the server 304 sends data to the PC 300 causing the PC 300 to display to the user a control 324 "service options" which requests the user to supply information identifying a level of service desired. Specifically, the service options control 324 allows the user to select service level among a set of levels. The various levels of service can vary based on content. For example the highest level allows access to all the content, such as live video streams, enabled GPS and on-line shopping functionality, weather information, breaking news, etc. The level that is immediately below the highest level provides all of that with the exception of the breaking news service. The lowest level of service can be limited to live video only. It will be plain to a person skilled in the art that the number of service levels offered to a user and the way those service levels are differentiated from one another is a matter of design and can vary widely without departing from the spirit of the invention.

Once the various service selections have been completed, the user activates the "pay" control 326. At that point, the server 304 will determine the amount of money the user is to be charged on the basis of the service level selection 324. Next, the server 304 will perform the payment step of the process. Two possible options exist. One is to charge the credit card provided by the user and that is currently on file or any other payment instrument that was provided. The other option is to send data to the PC 300 that will prompt the user to supply payment instrument information, such as a credit card to be charged. This payment instrument information will be processed by the server 304 to complete the payment step.

After the payment step has been completed, the server 304 will set up the electronic device 16 for the live sporting event for which service has been purchased. The set up includes the following:

The server 304 will download to the PC 300 the necessary service data, such as the data to set-up/alter the GUI of the electronic device 16 and/or cartographic data for the venue, assuming GPS functionality of the electronic device 16;

Ancillary data such as:
  Advertisement content;
  Venue or event related contextual content;
  Shopping information such as an on-line catalog;
  Trivia or surveys;
  Video games;
  Environmental/meteorological information;
  News
Authentication information In the case of the ancillary data, only the data that will be relevant or up to date when the event takes place should be downloaded. In order to make the ancillary data appear as if it is "spontaneously" available to the spectator during the event it may be designed to be available for viewing only when the user is at the event. For instance the data can be "hidden" from the user or designed in such as way that it cannot be accessed by the user unless a "trigger" is input by the electronic device 16. Such trigger can be specific data included in the wireless RF transmission that "unlocks" the hidden ancillary content. With this approach the ancillary data that is being downloaded to the PC 300, can be customized according to the profile of the user. More specifically, the information can be requested when creating the user account to submit preference information. This type of information was discussed previously. The server 304 determines on the basis of the preference information what kind of ancillary data to download.

The downloading of authentication information allows to securely set up the electronic device 16 for reception of services. For instance, the wireless RF transmission can be designed to be protected. The authentication information downloaded in the PC 300 and that is transferred to the handheld electronic device 16 allows to unlock the handheld electronic device 16 at the live sporting event. The authentication information can be in the form of a user code (as described below) or in the form of a decryption key (that can be unique to the electronic device 16 or common for all electronic devices 16 that subscribe for services for that particular live sporting event). The decryption key can be used to decrypt encrypted content in the wireless RF transmission.

Once all the data for setting up the electronic device 16 has been downloaded to the PC 300, the data is transferred to the electronic device 16 via the USB interface 104. At this point the electronic device 16 is ready for use. When activated by the spectator at the live sporting event, the electronic device 16 will pick up the wireless RF transmission and it will use the decryption key to adequately decode the data. Also, the electronic device 16 will also detect in the wireless RF transmission the "trigger" that will unlock for the spectator to see and access the latent ancillary data. Therefore, the spectator can see advertisement information, conduct on-line shopping etc.

The online transaction described earlier can be used as a mechanism to communicate to the server 304 the identity of the electronic device 16. So as users are performing on-line purchases of service delivery to the respective electronic devices 16, the server 304 is building a list of the electronic devices 16 that are authorized to receive the service. This list is kept a storage medium of the server 304, such as in a database (not shown). Just prior the live sporting event, the server 304 that holds in its database the list of all the electronic devices 16 (electronic identifiers) that have purchased service for the event, transfers the list to the authentication database 502. Those identifiers are then included in the wireless RF transmission as previously described.

The server 304 can also be designed to generate the user code described earlier, which the spectator needs to enter on the user interface of the handheld electronic device 16 in order to gain access to some or all of the content carried in the wireless RF transmission. The server implements the user code generator 1008 shown in FIG. 26. During the interaction between the PC 300 and the server 304, the electronic identifier 1002 is delivered to the server 304. The electronic identifier 1002 is extracted by the authentication processor 1006 of the handheld electronic device 16, communicated to the PC 300 and then transmitted to the server 304. The user code generator 1008 receives this information and processes it along with the event code (single code or compound code for multiple service levels) to produce a user code. In the case of a compound event code, which is made up of several different service level codes, the process is run several times with a different service level code at each cycle. The output of the process, which is a user code, is communicated back to the PC 300. The user code appears on the display of the PC 300 such that the user can take note of it and can print it or otherwise make note of it, or it can be sent in the form on an e-mail to the user to a specified e-mail address or via any other suitable method. The user code can also be loaded directly in the handheld electronic device 16 as described above. This obviates the need for the user to manually enter the user code at the handheld electronic device 16.

Note that in the case the user has created an account on the server 304, the electronic identifier 1002 may be stored in the account and there is no need to extract it from the handheld electronic device and communicate it to the server 304. In this form of implementation, the user logs on as described earlier and he/she automatically obtains the user code, that is computed by using the electronic identifier 1002 stored in the account and the event code.

Note that another possibility to deliver a user code is via a telephone system. Here the user dials a predetermined number and when prompted enters the on the dial pad the electronic identifier 1002. The user code generator at the telephone processing site generates a user code on the basis of the electronic identifier 1002 and the event code and communicates it to the user via voice synthesis. Also if an account for the user is created at the telephone processing site, the electronic identifier 1002 may be stored and there is no need to enter it again for each transaction.

In a possible variant the electronic device 16 can be designed with a wireless communication capability, such as via a Bluetooth technology of Wireless Fidelity (WiFi) technology to allow the electronic device 16 to communicate directly with the server 304 via any local wireless reception station also called "hot spots". In this fashion, the electronic device 16 does not require a connection to PC 300 to be set up by the server 304. Under this variant, all the commands and service selection choices can be made directly from the electronic device 16.

Note that when the electronic device 16 is provided with bidirectional communication capability, on-line purchases can be made by allowing the electronic device 16 to communicate over a cellular network with the server 304 over which the user record resides. Here, the on-line purchasing process is as described earlier, where the spectator attending the live sporting event chooses the product or service to buy and connects with the server 304 over the Internet 302 such as to complete the transaction. The transaction would include authenticating the user by providing a user ID and password. Assuming the payment instrument information and shipping information are already on record on the user account, the transaction completes.

Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. A handheld electronic device for use at a venue hosting a live sporting event, comprising:
   a) a receiver for receiving a wireless RF transmission conveying:
      i) a plurality of real-time video streams conveying live sporting event content, the live sporting event content including moving images of action occurring at the live sporting event held at the venue;
      ii) real-time physiological data associated with a player involved in the live sporting event held at the venue;
      iii) information that defines which of the plurality of real-time video streams the real-time physiological data is currently associated with, the real-time physiological data is associated with different ones of the plurality of real-time video streams at different times;
   b) a display;
   c) a user interface for selecting a real-time video stream among said plurality of real-time video streams to be displayed on said display;
   d) selecting one of a first real-time video stream and a second real-time video stream for real-time display wherein said handheld electronic device capable of overlaying the real-time physiological data on a first real-time video stream of said plurality of video streams when said information indicates that said real-time physiological data is associated with said first real-time video stream or said handheld electronic device capable of overlaying the real-time physiological data on a second real-time video stream of said plurality of real-time video streams when said real-time information indicates that said real-time physiological data is associated with said real-time second video stream.

2. A handheld electronic device as defined in claim 1, wherein at least two of the video streams are derived from cameras filming the live sporting event and convey different views of the action.

3. A handheld electronic device as defined in claim 2, wherein said physiological data conveys a heart rate.

4. A handheld electronic device as defined in claim 2, wherein said physiological data conveys a body temperature.

5. A handheld electronic device as defined in claim 3, wherein said live sporting event is a car race.

6. A handheld electronic device for use at a venue hosting a live sporting event, comprising:
   a receiver for receiving a wireless RF transmission conveying:
      i) a plurality of real-time video streams conveying live sporting event content, the live sporting event content including moving images of action occurring at the live sporting event held at the venue;
      ii) real-time physiological data is associated with a player involved in the live sporting event held at the venue including information defining which of the plurality of real-time video streams the real-time physiological data is associated with;
   a display;
   a storage medium for storing the real-time physiological data;
   a user interface for selecting a video stream among said plurality of real-time video streams to be displayed on said display;
   selecting the real-time video stream wherein said hand held electronic device capable of overlaying real-time physiological data on the real-time video stream of said plurality of real-time video streams when said information indicates that said real-time physiological data is associated with said real-time video stream and said real-time video stream is selected for display.

7. A handheld electronic device as defined in claim 6, wherein at least two of the video streams are derived from cameras filming the live sporting event and convey different views of the action.

8. A handheld electronic device as defined in claim 7, wherein said handheld electronic device is responsive to spectator inputs entered at said user interface to manipulate images of the video game on said display.

9. A handheld electronic device as defined in claim 8, wherein the video game data includes program code for execution by a processor of said handheld electronic device.

* * * * *

UNITED STATES PATENT AND TRADEMARK OFFICE
CERTIFICATE OF CORRECTION

PATENT NO. : 7,657,920 B2  Page 1 of 1
APPLICATION NO. : 11/459308
DATED : February 2, 2010
INVENTOR(S) : Arseneau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 248 days.

Signed and Sealed this

Thirtieth Day of November, 2010

David J. Kappos
*Director of the United States Patent and Trademark Office*